(12) United States Patent
Nagy

(10) Patent No.: US 8,343,926 B2
(45) Date of Patent: Jan. 1, 2013

(54) THERAPEUTIC STRATEGIES FOR PREVENTION AND TREATMENT OF ALZHEIMER'S DISEASE

(75) Inventor: Zsuzsanna Nagy, Oxford (GB)

(73) Assignee: Isis Innovation Ltd., Oxford (GB)

( * ) Notice: Subject to any disclaimer, the term of this patent is extended or adjusted under 35 U.S.C. 154(b) by 872 days.

(21) Appl. No.: 10/200,023

(22) Filed: Jul. 19, 2002

(65) Prior Publication Data

US 2003/0032673 A1 Feb. 13, 2003

(30) Foreign Application Priority Data

Jul. 19, 2001 (GB) .................................. 0117645.2

(51) Int. Cl.
*A61K 38/00* (2006.01)
*A61K 31/33* (2006.01)
(52) U.S. Cl. ........ 514/17.8; 514/183; 514/247; 514/766
(58) Field of Classification Search .................. 514/350, 514/766, 247, 183, 17.8
See application file for complete search history.

(56) References Cited

U.S. PATENT DOCUMENTS

| 5,663,201 | A | * | 9/1997 | Lowther et al. | ................ | 514/507 |
| 5,846,984 | A | * | 12/1998 | Greene et al. | .................. | 514/350 |
| 5,922,761 | A | * | 7/1999 | Lai | .................. | 514/476 |
| 6,147,094 | A | * | 11/2000 | Towart et al. | .................. | 514/332 |
| 6,264,994 | B1 | * | 7/2001 | Castillo et al. | ................ | 424/725 |

FOREIGN PATENT DOCUMENTS

| EP | EP 0 778 023 A1 | * | 11/1997 |
| EP | 1006108 A1 | | 6/2000 |
| EP | 1239038 A1 | | 3/2001 |
| GB | 2314268 A | | 12/1997 |
| WO | 9311762 | | 6/1993 |
| WO | 9400095 | | 1/1994 |
| WO | WO 94/00095 A | | 1/1994 |
| WO | 9609299 | | 3/1996 |
| WO | 9802435 | | 1/1998 |
| WO | WO 98/09523 A | | 3/1998 |
| WO | 9825887 | | 6/1998 |
| WO | 9847854 | | 10/1998 |
| WO | 9851702 | | 11/1998 |
| WO | 9937294 | | 7/1999 |
| WO | 9948489 | | 9/1999 |
| WO | 0019200 | | 4/2000 |
| WO | 0100619 A1 | | 1/2001 |
| WO | 0110829 A1 | | 2/2001 |
| WO | 0112236 A2 | | 2/2001 |
| WO | 0151464 A1 | | 7/2001 |
| WO | 0156982 A1 | | 8/2001 |
| WO | WO 02/073212 A2 | | 9/2002 |
| WO | 03083067 A2 | | 10/2003 |
| WO | 2004002488 A1 | | 1/2004 |

OTHER PUBLICATIONS

Biochem. Journal, 1999, 343, pp. 419-423.*

Arendt TH et al., Neuroprotection by repressing G0-G1 transition: A therapeutic strategy for AD? European Journal of Neuroscience, vol. 12, No. Supplement 11, 2000, p. 552 (XP001117411).
Copani, A., et al., Mitotic signaling by beta.-amyloid causes neuronal death. Faseb Journal (1999) 13/15 (2225-2234), (XP001106213).
Janicki, et al., "Presenilin Overexpression Arrests Cells in the G1 Phase of the Cell Cycle," Arrest Potentiated by the Alzheimer's Disease PS2(N1411) Mutant, Amer. Journal of Pathology, vol. 155, No. 1, Jul. 1999, pp. 135-144.
Kwada, Manabu et al., A noval antitumor compound, reduces cyclin D1 levels, arrests cell cycle at G1 phase, and inhibits anchorage-independent growth of human tumor cells, Experimental Cell Research (1999), 249(2), 240-247, 1999 (XP001107085.
Liu, et al., "Neuronal apoptosis at the G1/s cell cycle checkpoint," Cell Tissue Res, 305: 217-228, 2001.
Nagy, et al., "Cell cycle kinesis in lymphocytes in the diagnosis of Alzheimer's disease," Neuroscience Letters, 317: 81-84, 2002.
Nagy, et al., Cell cycle markers in the hippocampus in Alzheimer's diseae, (XP 002227838); Acta Neuropathology (1997) 94:6-15.
Nagy, et al., Expression of cell division markers in the hippocampus in Alzheimer's disease and other neuodegenerative conditions, Acta Neuropathol. 93: 294-300, 1997.
Nagy, et al., "The cell division cycle and the Pathophysiology of Alzheimer's Disease, "(XP-002227839), Neuroscience vol. 87, No. 4, pp. 731-739, 1998.
Nakai et al., "PKC and Tyrosine Kinase Involvement in Amyloid Beta (25-35)-Induced Chemotaxis of Microglia", Neuroreport, Rapid Communications of Oxford, vol. 9, No. 15, pp. 3467-3470 (1998).
Database WPI Week 199744, Derwent, AN 1997-475453 & JP 09 221421 (Kyowa Hakko Kogyo KK) (Aug. 26, 1997).
Chyan et al., "Neuroprotective Activity of Melatonin Against Alzheimer Beta-Amyloid is Not Mediated by Melatonin Receptors",Society of Neuroscience Abstracts, vol. 24, No. 1/2, p. 1455, (Nov. 1998).
Database WPI Week 200114, Derwent, AN 2001-127322 & JP 2000 290184 (Kyowa Hakko Kogyo KK) (Oct. 17, 2000).
Racchi et al., "Bradykinin Induced Amyloid Precursor Protein Secretion in Fibroblasts from Alzheimer's Disease, Down's Syndrome and Control Donors", Society of Neuroscience Abstracts, vol. 22, No. 1-3, p. 1944 (Nov. 1996).
Giovanni et al., "Involvement of Cell Cycle Elements, Cyclin-dependent Kinases, pRb, and E2F-DP, in B-amyloid-induced Neuronal Death", J. Biol. Chem., vol. 274, No. 27, pp. 19011-19016 (Jul. 1999).
Giovanni et al., "E2F1 Mediates Death of B-amyloid-treated Cortical Neurons in a Manner Independent of p53 and Dependent on Bax and Caspase 3", J. Biol. Chem., vol. 275, No. 16, pp. 11553-11560 (Apr. 2000).
Israel et al., Discrimination Between Ventricular and Spraventricular Tachycardia by Dual Chamber Cardioverter Defibrillators: Importance of the Atrial Sensing Function, PACE—Pacing and Clinical Electrophysiology, vol. 24, No. 2. pp. 183-190 (2001).

(Continued)

*Primary Examiner* — Sreeni Padmanabhan
*Assistant Examiner* — Shobha Kantamneni
(74) *Attorney, Agent, or Firm* — Jeffrey I. Auerbach; The Auerbach Law Firm, LLC

(57) ABSTRACT

The invention relates to therapeutic agents for use in the prevention or treatment of Alzheimer's disease. In particular the invention relates to use of inhibitors of cell cycle re-entry and progression to the G1/S transition or inhibitors of progression of the cell cycle through the G1/S transition point in the prevention or treatment of Alzheimer's disease.

7 Claims, 11 Drawing Sheets

OTHER PUBLICATIONS

Lazarovici et al. "K252a and Staurosporine Microbial Alkaloid Toxins as Prototype of Neurotropic Drugs", Advances in Experimental Medicine & Biology, vol. 391, pp. 367-377 (1996).
Crapper Mclachlan et al., "Intramuscular Desferrioxamine in Patients with Alzheimer's Disease", The Lancet, vol. 337, No. 8753, pp. 1304-1308 (Jun. 1991).
Nitsch et al., "Vasopressin and Bradykinin Regulate Secretory Processing of the Amyloid Protein Precursor of Alzheimer's Disease", Neurochemical Research, vol. 23, No. 5, pp. 807-814 (1998).
Pappolla et al., "Melatonin Prevents Death of Neuroblastoma Cells Exposed to the Alzheimer Amyloid Peptide", J. of Neuroscience, vol. 17, No. 5, pp. 1683-1690 (Mar. 1997).
Regenold et al., "Uses of Intravenous Valproate in Geriatric Psychiatry", Am. J. of Geriatric Psychiatry, vol. 9, No. 3, pp. 306-308 (2001).
Sival et al., "The Effects of Sodium Valproate on Disturbed Behavior in Dementia", J. of American Geriatrics Society, vol. 42, No. 8, pp. 906-907 (1994).
Takahashi et al., "Shorei Hokoku Valproic Acid Natrium . . . ", Brain and Nerve, vol. 48, No. 8, pp. 757-760 (1996).
Search Report dated Jun. 13, 2007 for Application No. EP 06025392.
Search Report dated Apr. 26, 2007 for Application No. EP 06025393.
Search Report dated May 30, 2007 for Application No. EP 06025394.
European Search Report (EP 06 02 5392); Date of Completion Feb. 6, 2007; 2 Pages.

* cited by examiner

Fig. 1a. The effect of different drugs on cell survival and proliferation
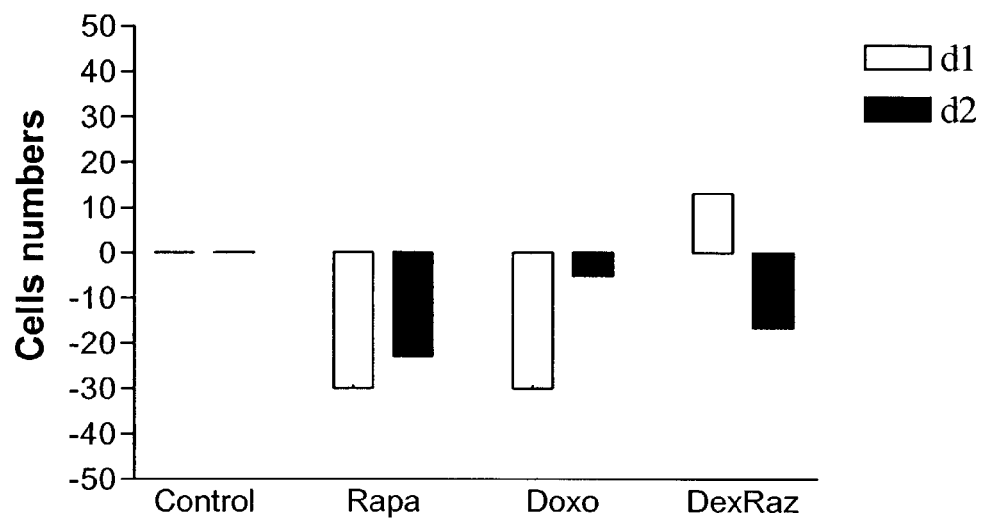
Fig. 1b. The effects of oxidative stress on cell survival and proliferation
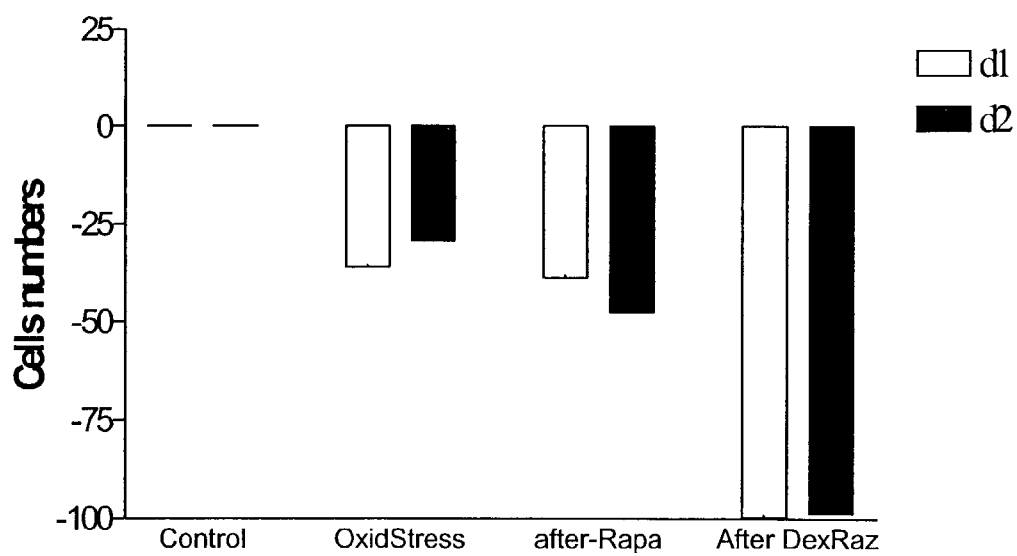

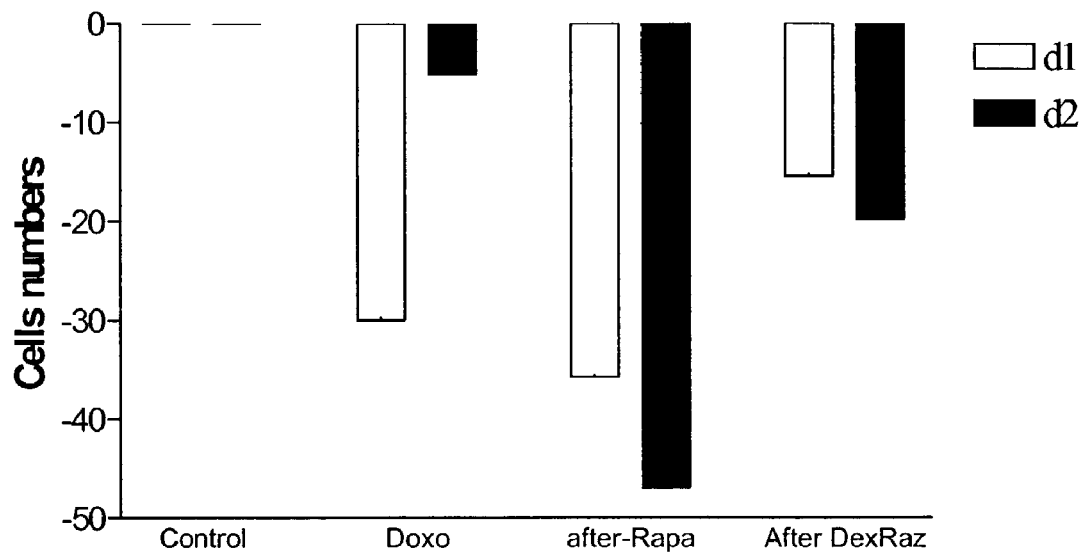
Fig. 1c. The effects of Doxorubicine on cell survival and proliferation
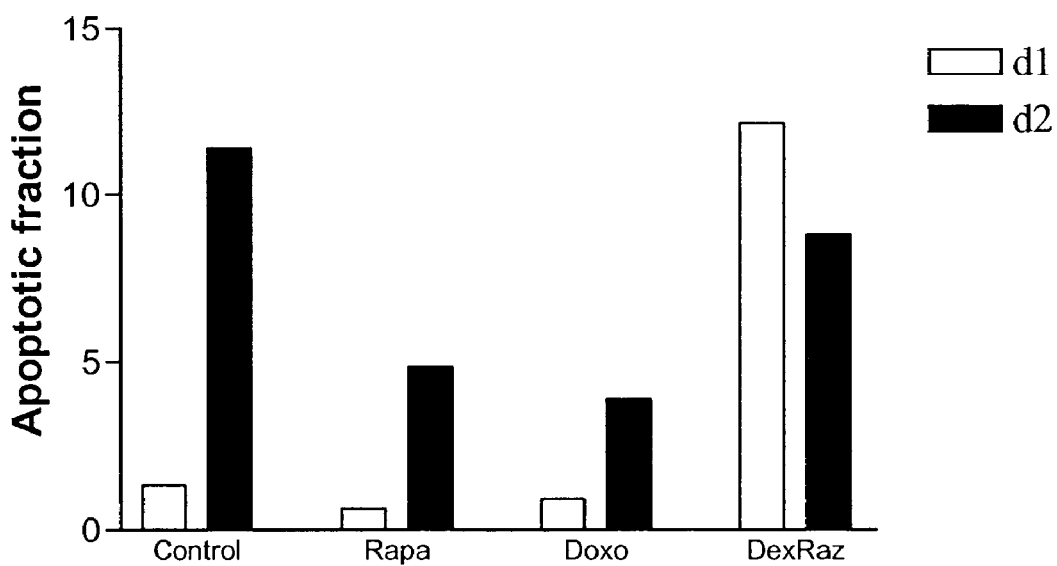
Fig. 2a. The effect of cell cycle regulator drugs on Apoptosis Fig. 2b. The effects of oxidative stress on apoptosis
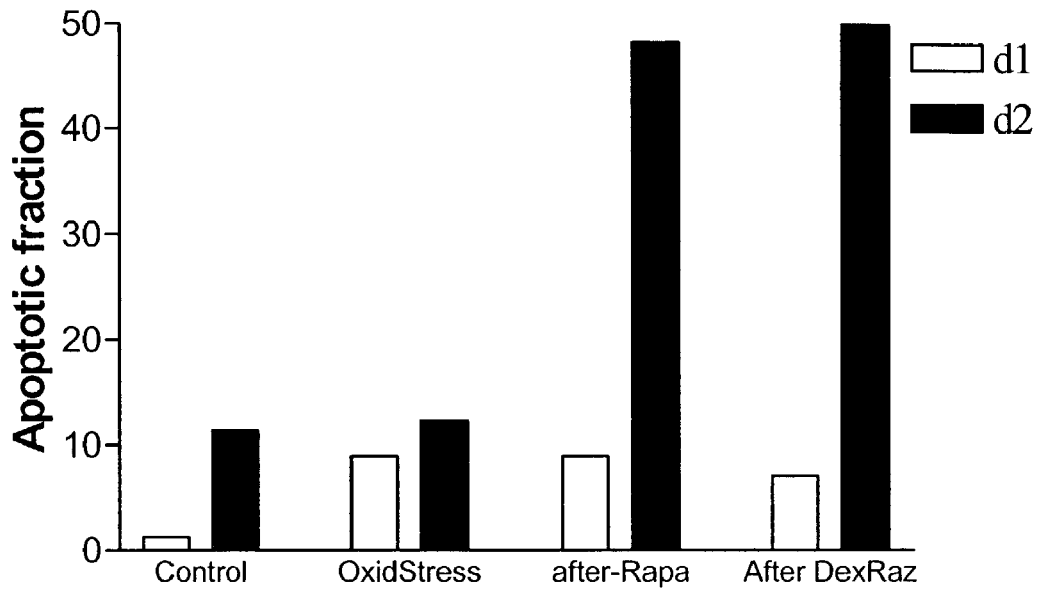
Fig. 2c. The effects of doxorubicine on apoptosis
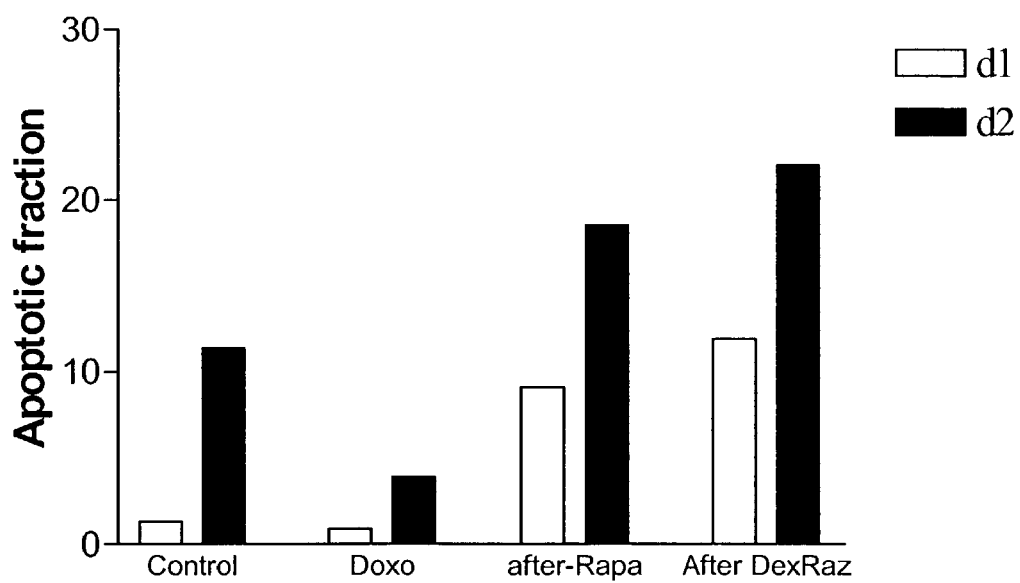

Fig. 3a. The effect of various drugs on the length of the G1 phase of the cell cycle
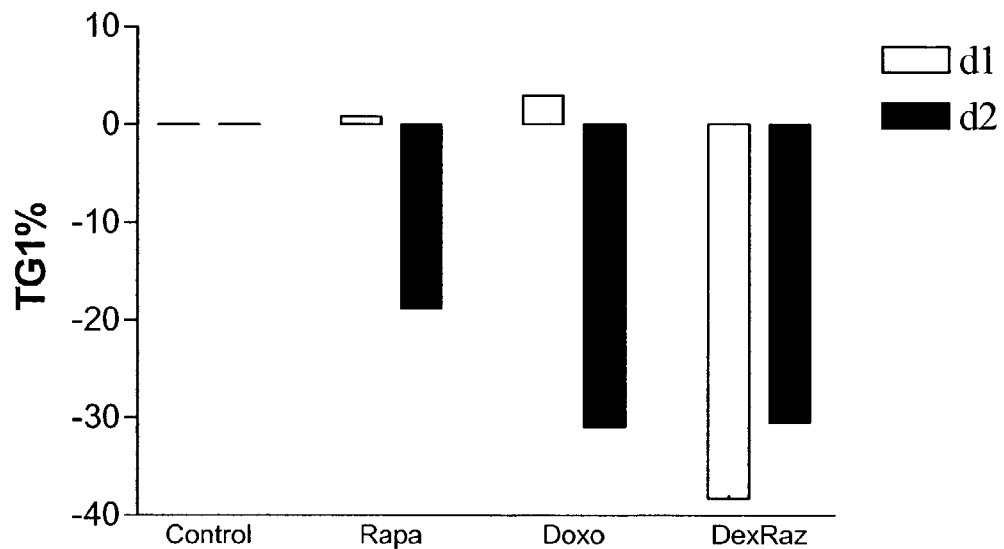
Fig. 3b. The effect of sub-lethal oxidative stress on the length of the G1 phase of the cell cycle
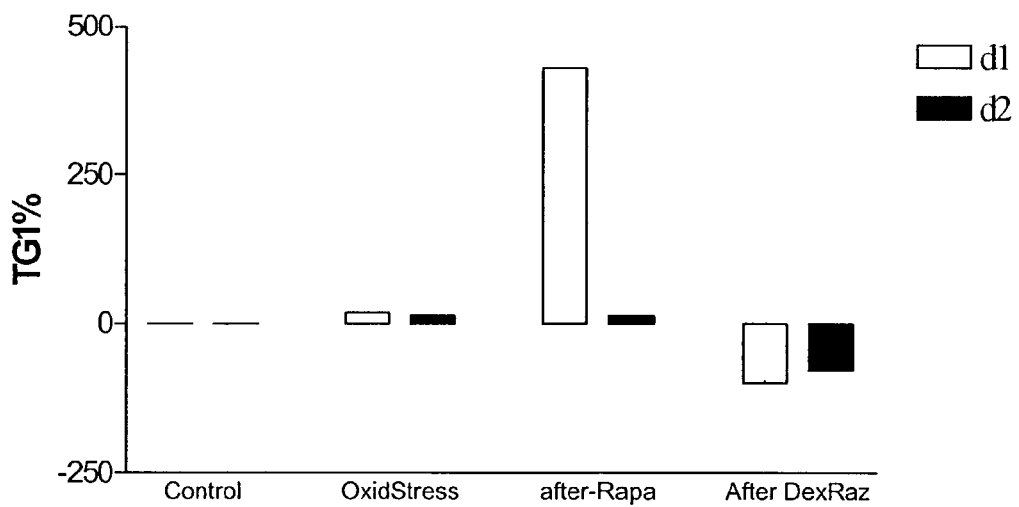

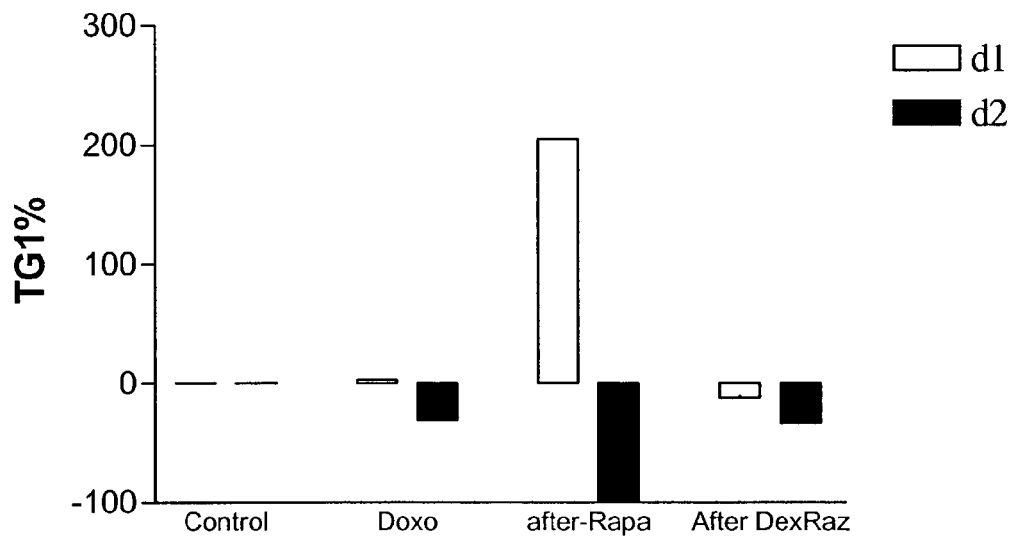
Fig. 3c. The effect of doxorubicine on the length of the G1 phase of the cell cycle
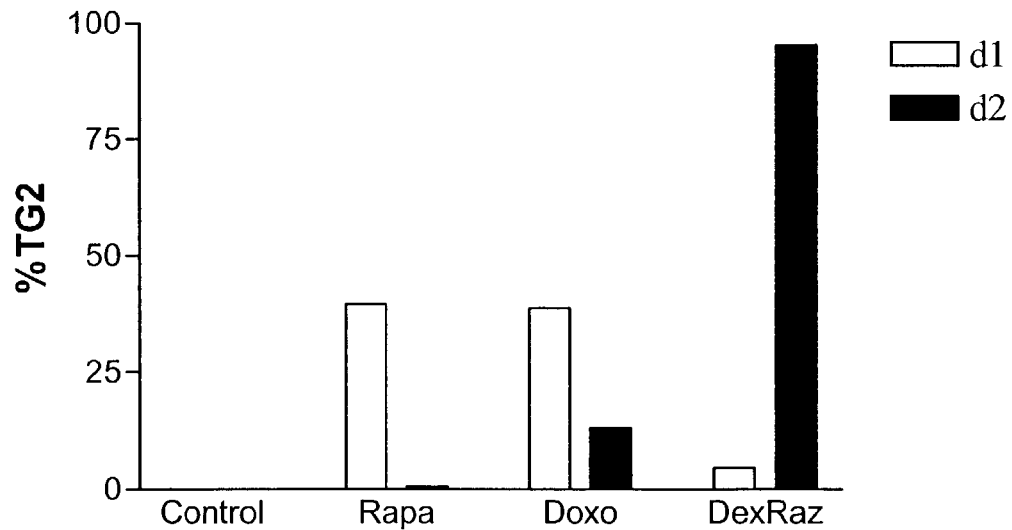
Fig. 4a. The relative change of G2 length under the effect of cell cycle inhibitors

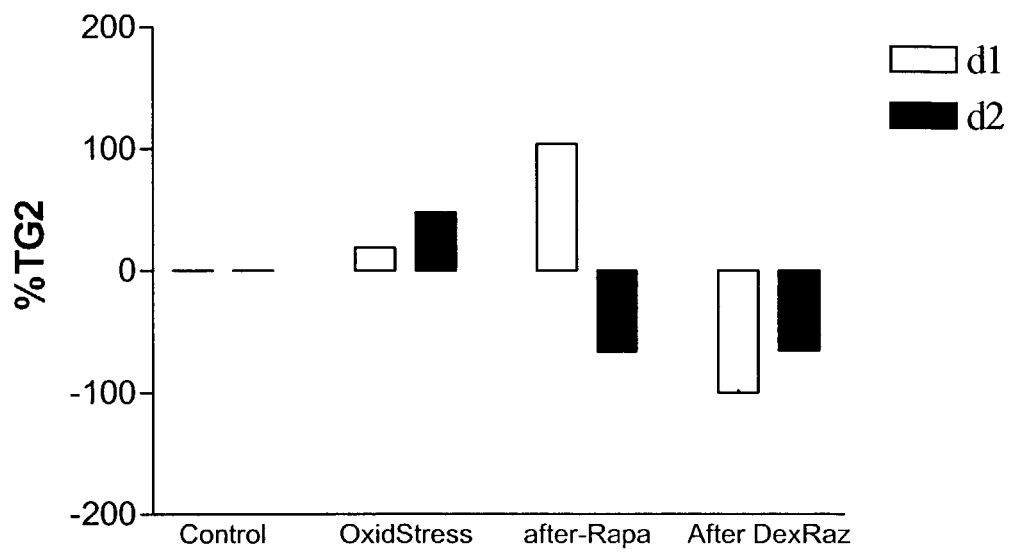
Fig. 4b. The relative change of G2 length under the effect of oxidative stress
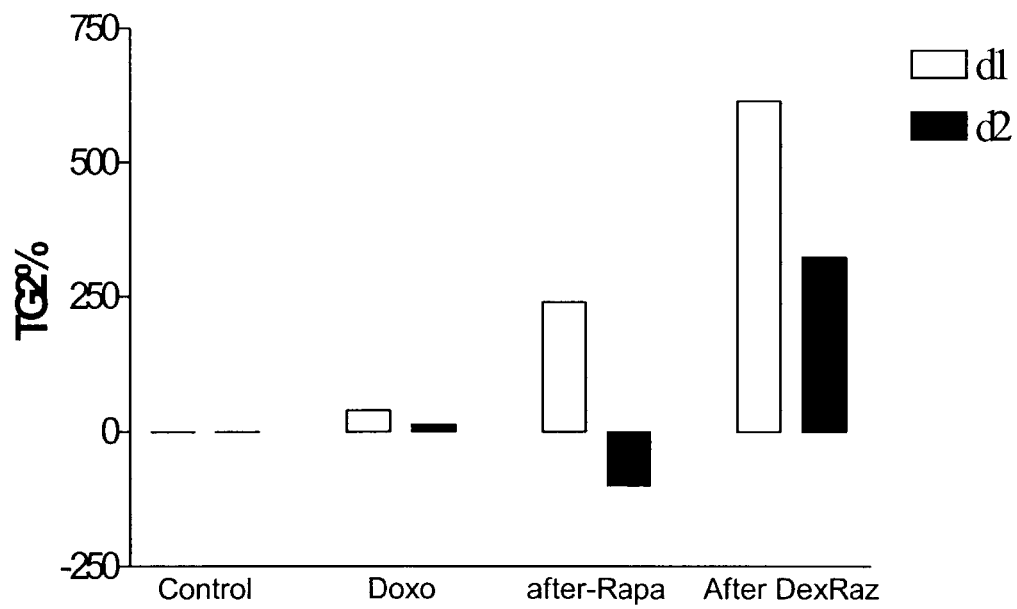
Fig. 4c. The relative change of G2 length under the effect of doxorubicine

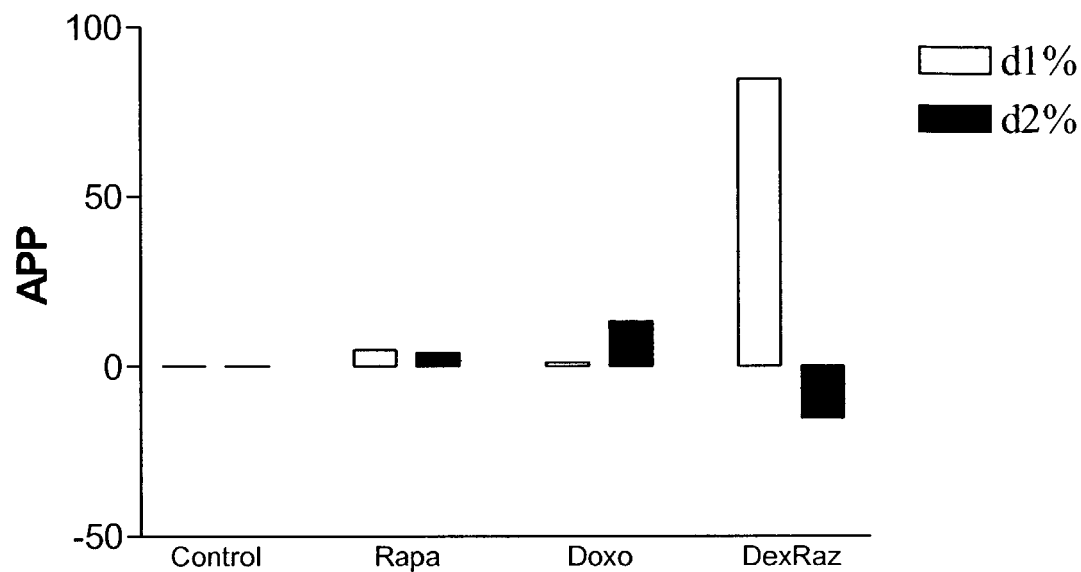
Fig. 5a. The effect of cell cycle inhibitor drugs on APP expression
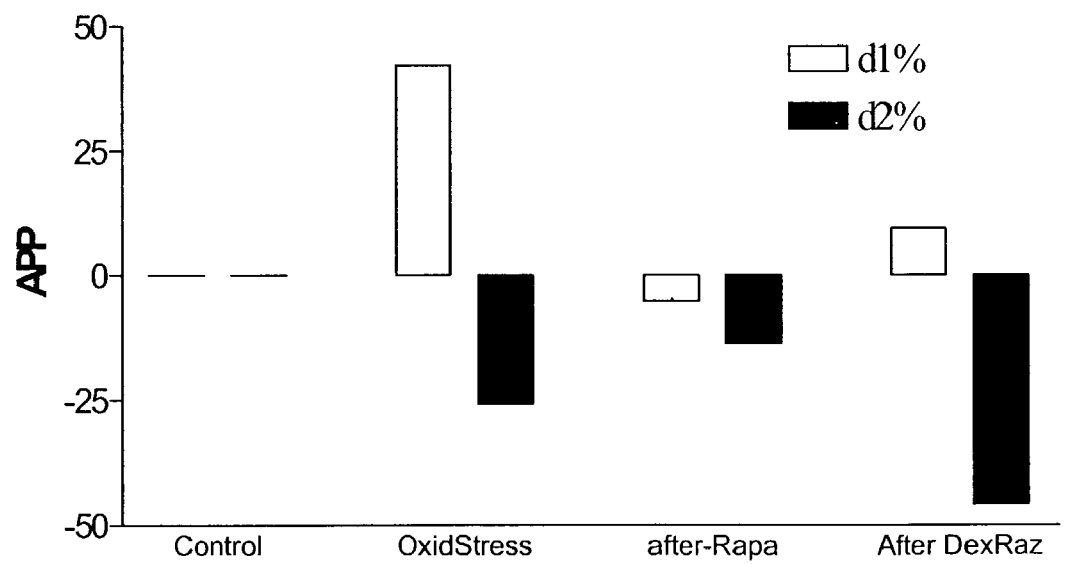
Fig. 5b. The effect of oxidative stress on APP expression Fig. 5c. The effect of doxorubicine on APP expression
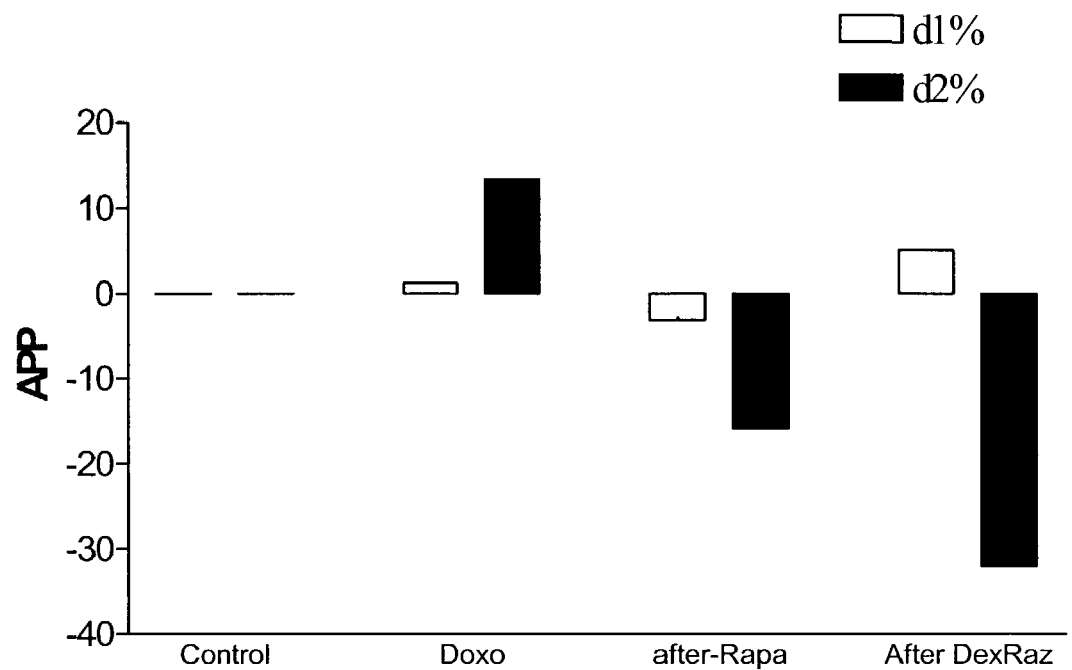
Fig. 6a. The effect of cell cycle inhibitor drugs on the expression of AD-type hyperphosphorylated tau
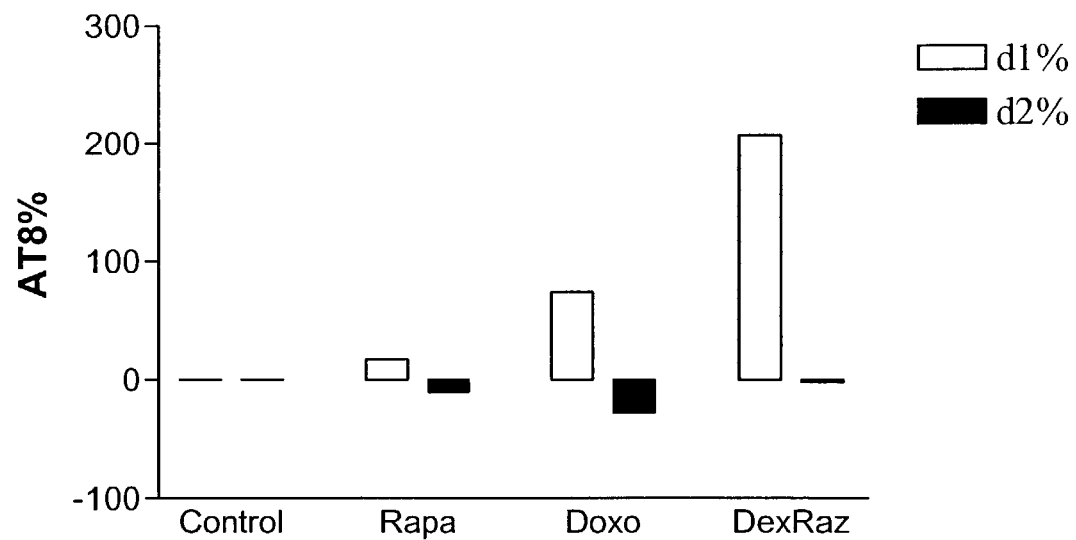

Fig. 6b. The effect of oxidative stress on the expression of AD-type hyperphosphorylated tau
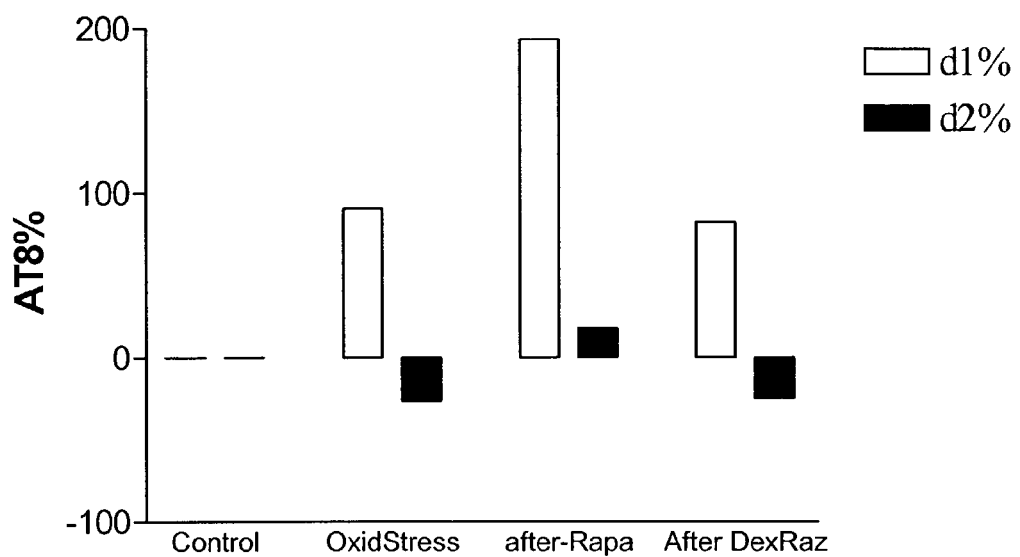
Fig. 6c. The effect of doxorubicine on the expression of AD-type hyperphosphorylated tau
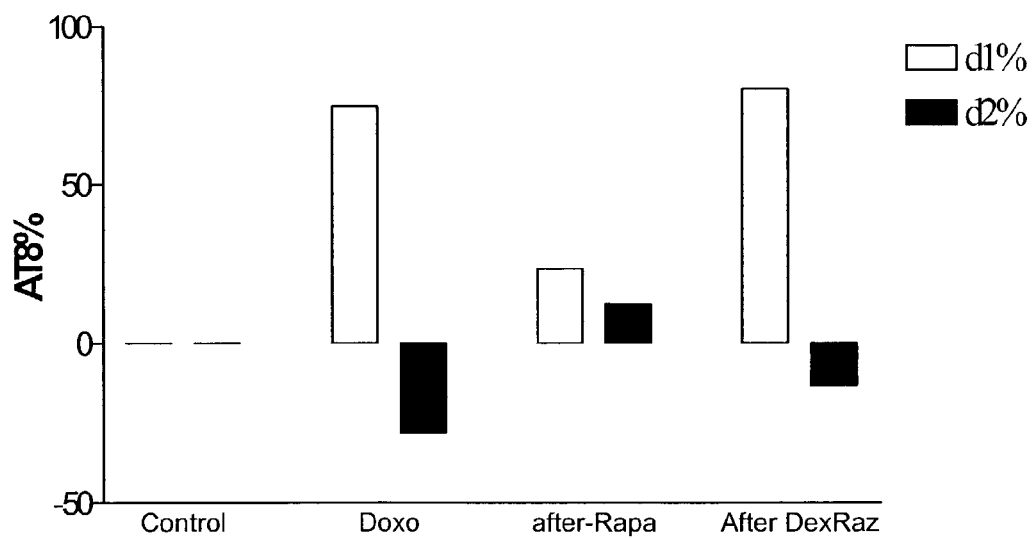

Fig. 7a. The effect of cell cycle inhibitor drugs on the expression of AD-type PHF tau
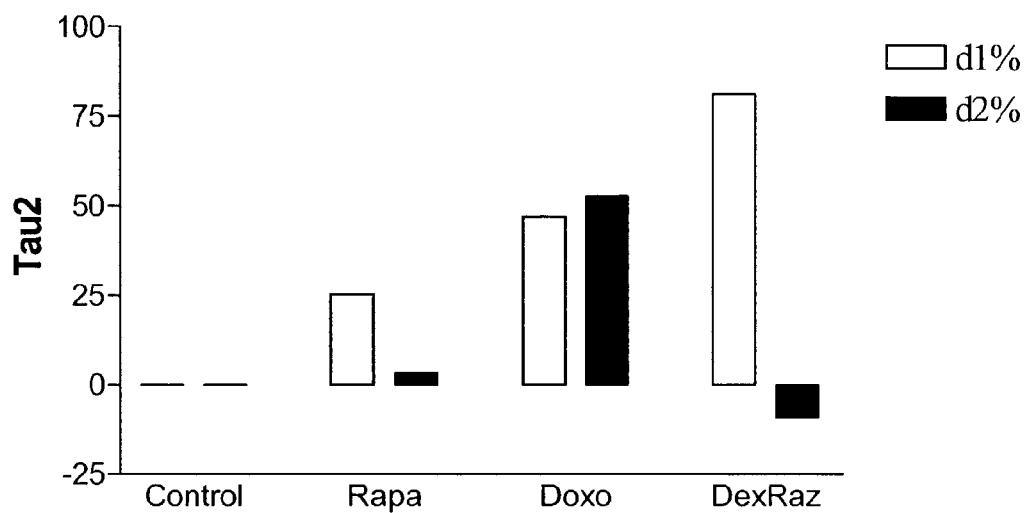
Fig. 7b. The effect of oxidative stress on the expression of AD-type PHF tau
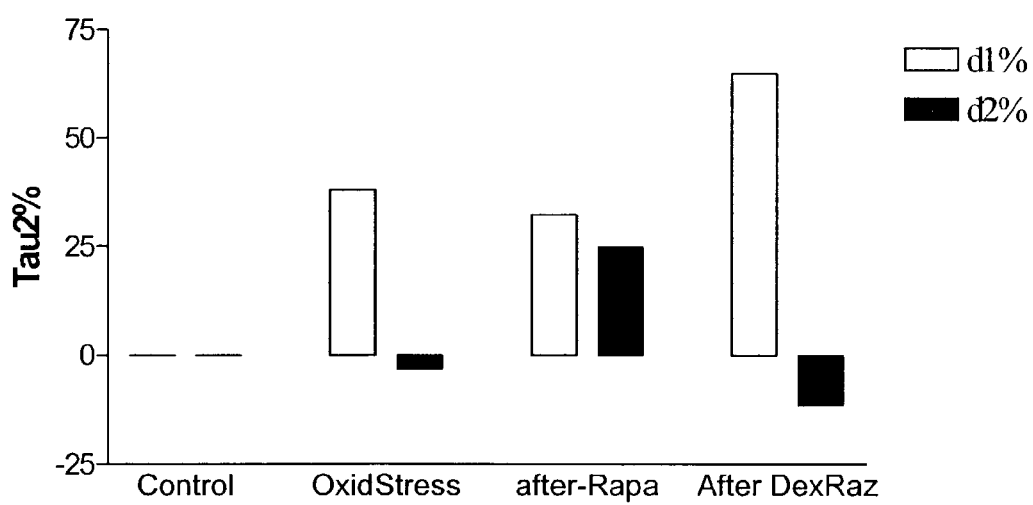

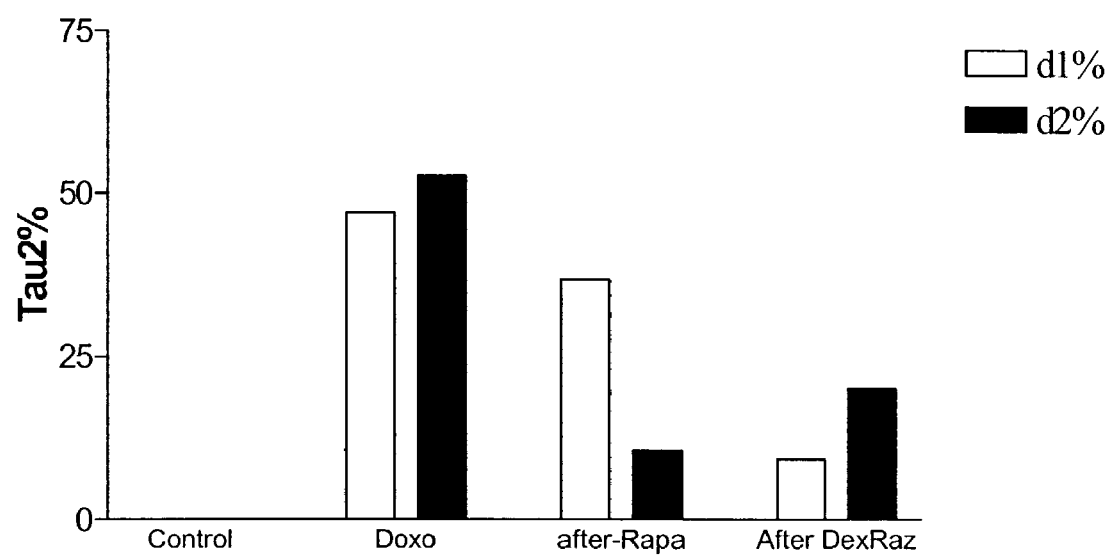
Fig. 7c. The effect of doxorubicine on the expression of AD-type PHF tau

THERAPEUTIC STRATEGIES FOR PREVENTION AND TREATMENT OF ALZHEIMER'S DISEASE

FIELD OF THE INVENTION

The present invention relates to novel strategies for treatment and prevention of Alzheimer's disease.

BACKGROUND OF THE INVENTION

As life expectancy increases Alzheimer's disease (AD) is becoming a major health problem in the western world. There has been intensive research aimed at identifying a reliable cure or preventive measures for the disease, so far without success.

Currently there are two mainstream therapeutic approaches to the treatment of Alzheimer's disease. The first is treatment with acetylcholine esterase inhibitors, which reduce the effects of neuron loss in the central nervous system and therefore provide some symptomatic relief for the cognitive defects. However, this approach is appropriate only in those patients in which there is substantial functional reserve left in the brain.

The second approach is to reduce the amount of or stop the deposition of beta-amyloid plaques in the brain. The main drawback of this approach is that amyloid deposition is not the cause but rather a consequence of Alzheimer's disease, and the accumulation of this protein does not have any effect on the cognitive status or functional capacity of the brain.

In recent years it is becoming more widely accepted that the pathogenic basis of Alzheimer's disease is the aberrant re-entry of different neuronal populations into the cell division cycle (Nagy Z, Esiri M M and Smith A D (1998) *Neuroscience* 84: 731-739). In healthy elderly individuals rapid cell cycle arrest and re-differentiation may follow this cell cycle re-entry. In contrast, in individuals with Alzheimer's disease the regulatory mechanisms appear to fail and the neurons progress into the late stages of the cell cycle leading to the accumulation of AD-related pathology and/or neuronal death (Nagy Z, Esiri M M and Smith A D (1998) *Neuroscience* 84: 731-739).

Studies by the present inventors and others indicate that the cell cycle regulatory failure in Alzheimer's disease occurs at the G1/S transition checkpoint (Arendt T, Rodel L, Gartner U and Holzer M (1996) *Neuroreport* 7: 3047-9). Previous studies on fibroblasts and lymphocytes from Alzheimer's disease patients indicate that the regulation of the cell division cycle might be disrupted in cells other than neurons in this condition (Eckert A, Hartmann H, Forstl H and Muller W E (1994) *Life Sci* 55: 2019-29; Fischman H K, Reisberg B, Albu P, Ferris S H and Rainer J D (1984) *Biol Psychiatry* 19: 319-27; Tatebayashi Y, Takeda M, Kashiwagi Y, Okochi M, Kurumadani T, Sekiyama A, Kanayama G, Hariguchi S and Nishimura T (1995) *Dementia* 6: 9-16). It is also known that Alzheimer's disease patients are more prone to some forms of cancer (Burke W J, McLaughlin J R, Chung H D, Gillespie K N, Grossberg G T, Luque F A and Zimmerman J (1994) *Alzheimer Dis Assoc Disord* 8: 22-8) and that Down's syndrome patients, who develop AD in early adult life, are more prone to leukaemia than the general population (Drabkin H A and Erickson P (1995) *Prog Clin Biol Res* 393: 169-76; Fong C T and Brodeur G M (1987) *Cancer Genet Cytogenet* 28: 55-76). It is plausible therefore to hypothesize that the cell cycle regulatory failure in neurons, even in early (pre-clinical) stages of AD, might be reflected by similar cell cycle regulatory malfunction in lymphocytes.

SUMMARY OF THE INVENTION

The present inventor has shown that the in vitro responsiveness of lymphocytes to G1 inhibitor treatment is significantly less effective in Alzheimer's disease patients than in control subjects. Additionally, in subjects showing clinical signs of incipient Alzheimer's disease the lymphocyte response is similar to that seen in Alzheimer's disease patients. These findings represent direct evidence that failure of the G1/S transition control is not restricted to neurons in Alzheimer's disease patients, but also occurs in peripheral cells, such as lymphocytes.

The two main targets of therapeutic intervention identified by the inventor are to prevent/inhibit cell cycle re-entry and progression to the G1/S transition point, or to prevent/inhibit the cell cycle progression at the G1/S transition point.

According to one aspect of the invention, methods of treating or preventing Alzheimer's disease in a human patient are provided. The methods include administering to a human patient in need thereof an effective amount of one or more inhibitors of cell cycle re-entry and progression to the G1/S transition. In certain embodiments, the inhibitor of cell cycle re-entry and progression to the G1/S transition is an inhibitor of the G0/G1 transition, and in other embodiments the inhibitor of cell cycle re-entry and progression to the G1/S transition induces cell cycle arrest in the G0/G1 phase.

Preferred inhibitors of cell cycle re-entry and progression to the G1/S transition for use in the foregoing methods include NA22598, sodium valproate, fascaplysin and brefeldin A.

According to another aspect of the invention, additional methods of treating or preventing Alzheimer's disease in a human patient are provided. The methods include administering to a human patient in need thereof an effective amount of one or more inhibitors of progression of the cell cycle through the G1/S transition point. In some embodiments, the inhibitor of progression of the cell cycle through the G1/S transition point blocks cell cycle progression in G1, and/or induces cell cycle arrest in G1, and/or induces cell cycle arrest at the G1/S checkpoint, and/or blocks the G1/S transition, and/or inhibits DNA synthesis.

Preferred inhibitors of progression of the cell cycle through the G1/S transition point include squamocin, peptide aptamers which specifically inhibit E2F binding activity, manumycin A, indole carbazole K252a, 4-sodium phenyl butyrate, retinoids or retinoid receptor selective ligands, combinations of oncostatin M and interleukin 6, an ansamycin (preferably herbimycin, geldanamycin or TT-B), vitamin D analogs, steroids or glucocorticoids, alpha adrenergic receptor antagonists (preferably doxazosin), iron chelators (preferably O-Trensox, desferrioxamine, an aroylhydrazone ligand, dexrazoxane or EDTA), angiotensin II receptor antagonists (preferably bradykinin), immunosuppressive chemotherapeutic drugs (preferably doxorubicin, adriamycin, rapamycin, cyclosporin A, FK506 or a prodigiosin), and melatonin.

The foregoing inhibitors of cell cycle re-entry and progression to the G1/S transition and inhibitors of progression of the cell cycle through the G1/S transition point can be administered alone or in combination with other of these inhibitors, or in combination with one or more non-cell cycle therapeutic agents for treating Alzheimer's disease, such as acetylcholine esterase inhibitors (such as donepezil, rivastigmine and galantamine), beta- and gamma-secretase inhibitors, Abeta vaccines, Cu—Zn chelators, cholesterol-lowering drugs and non-steroidal anti-inflammatory drugs. Preferred combinations of cell cycle therapeutic agents include doxorubicin and rapamycin (particularly administration of the rapamycin followed by the administration of the doxorubicin), and dexrazoxane and doxorubicin (particularly administration of the dexrazoxone followed by the administration of the doxorubicin).

According to a further aspect of the invention, methods of selecting a pharmaceutical agent for use in the treatment Alzheimer's disease in a human patient are provided. The methods include the steps of (a) exposing cells from the patient, which cells are non-neuronal cells that exhibit a cell cycle regulatory defect at the G1/S phase transition, to a panel of pharmaceutical agents which are known inhibitors of cell cycle re-entry and progression to the G1/S transition or known inhibitors of progression of the cell cycle through the G1/S transition point, (b) analyzing the regulation of the G1/S transition the cells in the presence and absence of the pharmacological agents, and (c) identifying an agent which corrects the regulatory defect at the G1/S transition in the cells, which agent is identified as likely to be of benefit in the treatment of Alzheimer's disease in the patient. In some embodiments, the panel of pharmaceutical agents includes one or more inhibitors of cell cycle re-entry and progression to the G1/S transition and/or one or more inhibitors of progression of the cell cycle through the G1/S transition point as described herein.

In another aspect of the invention, methods of screening compounds for potential pharmacological activity in the treatment of Alzheimer's disease are provided. The methods include contacting SH-SY5Y neuroblastoma cells with candidate compounds and testing for at least one parameter indicative of Alzheimer's disease pathology selected from the group consisting of: (i) cell survival and proliferation, (ii) apoptosis, (iii) relative lengthening of the G1 phase of the cell cycle, (iv) relative lengthening of the G2 phase of the cell cycle, (v) expression of amyloid precursor protein (APP), (vi) expression of hyperphosphorylated tau protein, and (vii) expression of PHF tau protein. Candidate compounds which cause a reduction in the tested parameter(s), as compared to control cells not exposed to the candidate compound, are scored as having potential pharmacological activity in the treatment of Alzheimer's disease.

In some embodiments, the candidate compound to be tested using the method is a known inhibitor of cell cycle re-entry and progression to the G1/S transition or a known inhibitor of progression of the cell cycle through the G1/S transition point.

According to yet another aspect of the invention, pharmaceutical kits for treating Alzheimer's disease are provided. The kits include a therapeutically effective amount of one or more cell cycle therapeutic agents for treating Alzheimer's disease selected from one or more inhibitors of cell cycle re-entry and progression to the G1/S transition and/or inhibitors of progression of the cell cycle through the G1/S transition point. In certain embodiments, combinations of cell cycle therapeutic agents are provided in the kits, such as doxorubicin and rapamycin, or dexrazoxone and doxorubicin. In other embodiments, the kits can also include a non-cell cycle therapeutic agent for treating Alzheimer's disease. The kits preferably also will contain instructions for simultaneous, separate or sequential administration of the cell cycle therapeutic agent and optionally the non-cell cycle therapeutic agent for treating Alzheimer's disease.

These and other embodiments of the invention are described in greater detail below.

BRIEF DESCRIPTION OF THE DRAWINGS

In FIGS. 1a, 2a, 3a, 4a, 5a, 6a and 7a, cells were treated with rapamycin (Rapa), doxorubicin (Doxo) or dexrazoxone (DexRaz). In FIGS. 1b, 2b, 3b, 4b, 5b, 6b and 7b, cells were subject to oxidative stress alone or following pre-treatment with rapamycin or dexrazoxone. In FIGS. 1c, 2c, 3c, 4c, 5c, 6c and 7c, cells were treated with doxorubicin alone, or following treatment with rapamycin or dexrazoxone. Various effects of the indicated treatments were measured on day 1 (d1) and day 2 (d2).

FIG. 1 illustrates the effects of cell cycle inhibitor drugs and oxidative stress on cell survival and proliferation, as measured using an MTT proliferation assay. FIG. 1a shows the effect of different drugs on cell survival and proliferation. FIG. 1b shows the effects of oxidative stress on cell survival and proliferation. FIG. 1c shows the effects of doxorubicine on cell survival and proliferation.

FIG. 2 illustrates the effects of cell cycle inhibitor drugs and oxidative stress on apoptosis, as measured using FACS analysis. FIG. 2a shows the effect of cell cycle regulator drugs on apoptosis. FIG. 2b shows the effects of oxidative stress on apoptosis. FIG. 2c shows the effects of doxorubicine on apoptosis.

FIG. 3 illustrates the effects of cell cycle inhibitor drugs and oxidative stress on length of the G1 phase of the cell cycle. The y-axis is relative lengthening of the G1 phase of the cell cycle expressed as a percentage. FIG. 3a shows the effect of various drugs on the length of the G1 phase of the cell cycle. FIG. 3b shows the effect of sub-lethal oxidative stress on the length of the G1 phase of the cell cycle. FIG. 3c shows the effect of doxorubicine on the length of the G1 phase of the cell cycle.

FIG. 4 illustrates the effects of cell cycle inhibitor drugs and oxidative stress on length of the G2 phase of the cell cycle. The y-axis is relative lengthening of the G3 phase of the cell cycle expressed as a percentage. FIG. 4a shows the relative change of G2 length under the effect of cell cycle inhibitors. FIG. 4b shows the relative change of G2 length under the effect of oxidative stress. FIG. 4c shows the relative change of G2 length under the effect of doxorubicine.

FIG. 5 illustrates the effects of cell cycle inhibitor drugs and oxidative stress on expression of amyloid precursor protein (APP). The y-axis is percent increase in the amount of protein relative to untreated control culture. The absolute values used to perform this analysis were derived from optical density measurements (OD) obtained from the ELISA assay performed. FIG. 5a shows the effect of cell cycle inhibitor drugs on APP expression. FIG. 5b shows the effect of oxidative stress on APP expression. FIG. 5c shows the effect of doxorubicine on APP expression.

FIG. 6 illustrates the effects of cell cycle inhibitor drugs and oxidative stress on expression of AD-type hyperphosphorylated tau. The y-axis is percent increase in the amount of protein relative to untreated control culture. The absolute values used to perform this analysis were derived from optical density measurements (OD) obtained from the ELISA assay performed. FIG. 6a shows the effect of cell cycle inhibitor drugs on the expression of AD-type hyperphosphorylated tau. FIG. 6b shows the effect of oxidative stress on the expression of AD-type hyperphosphorylated tau. FIG. 6c shows the effect of doxorubicine on the expression of AD-type hyperphosphorylated tau.

FIG. 7 illustrates the effects of cell cycle inhibitor drugs and oxidative stress on expression of AD-type PHF tau. The y-axis is percent increase in the amount of protein relative to untreated control culture. The absolute values used to perform this analysis were derived from optical density measurements (OD) obtained from the ELISA assay performed. FIG. 7a shows the effect of cell cycle inhibitor drugs on the expression of AD-type PHF tau. FIG. 7b shows the effect of oxidative stress on the expression of AD-type PHF tau. FIG. 7c shows the effect of doxorubicine on the expression of AD-type PHF tau.

DETAILED DESCRIPTION OF THE INVENTION

The invention relates to several strategies for therapeutic intervention in order to arrest progression of Alzheimer's disease or to prevent its development.

The two main targets of therapeutic intervention identified by the inventor are to prevent/inhibit cell cycle re-entry and progression to the G1/S transition point, or to prevent/inhibit the cell cycle progression at the G1/S transition point. Neuronal cell cycle re-entry can be prevented by therapies that act as differentiation factors or by interventions that reinforce synaptic connections and therefore the differentiated state of neurons. Therapies aimed at arresting the progression of the cell division cycle at the G1/S transition point include treatment with classical inhibitors of cell division, for example drugs used in cancer therapy and chemo-prevention.

The preferred agent for treatment of Alzheimer's disease in any given patient will vary depending on the precise nature of the underlying cell cycle regulatory defect present in that patient. It is not the case that all agents that prevent cell cycle re-entry and progression to the G1/S transition point, or which prevent the cell cycle progression at the G1/S transition point, will be effective in all Alzheimer's patients. The inventor's finding that the failure of the G1/S transition control is not restricted to neurons in Alzheimer's disease patients, but also occurs in peripheral cells, such as lymphocytes, has led to the development of an in vitro assay which can be used to identify and select agents which are effective in a particular patient. The ability to select an agent that will work in a given patient via a simple in vitro test is absolutely critical. Prior to the development of this in vitro screen it would simply not have been possible to select an agent having clinical utility in a particular patient without extensive, ethically unacceptable, "trial and error" in that patient.

In summary, the development of an in vitro screen which can be used identify agents capable of correcting the cell cycle regulatory defects present in Alzheimer's patients has made it possible for the first time to provide effective treatment and prophylaxis for Alzheimer's disease based on prevention/inhibition of cell cycle re-entry and progression to the G1/S transition point, or on prevention/inhibition of cell cycle progression at the G1/S transition point.

Therefore, in a first aspect the invention relates to use of at least one substance which is an inhibitor of cell cycle re-entry and progression to the G1/S transition for the manufacture of a medicament for the treatment or prevention of Alzheimer's disease.

The invention is also directed to method of treating or preventing Alzheimer's disease in a human patient comprising administering to a human patient in need thereof an effective amount of an inhibitor of cell cycle re-entry and progression to the G1/S transition.

Inhibitors of cell cycle re-entry and progression to the G1/S transition may act via various mechanisms, for example inhibition of the G0/G1 transition, or induction of cell cycle arrest in the G0/G1 phase.

Preferably the inhibitor of cell cycle re-entry and progression to the G1/S transition will be a substance that, when assessed using the in vitro assay described herein, produces significant correction of the cell cycle regulatory defect at the G1/S transition in an Alzheimer's patient, most preferably the Alzheimer's patient which it is intended to treat using the substance.

Preferred known inhibitors of cell cycle re-entry and progression to the G1/S transition, which may be used in accordance with this aspect of the invention, include the following, however this is not to be construed as limiting the invention to these specific embodiments:

NA22598—an anticancer drug that inhibits G0/G1 transition (Kawada, M., Kuwahara, A., et al. (1999) *Exp Cell Res*, 249(2): 240-247).

Sodium valproate and its derivatives—an inhibitor of the growth of human neuroblastoma cells and known antiepileptic agent (Cinatl, J. Jr., Cinatl, J., et al. (1997) *Anticancer Drugs,* 8(10): 958-963; Cinatl, J. Jr., Cinatl, J., et al. (1996) *Anticancer Drugs,* 7(7): 766-773).

Fascaplysin—which specifically inhibits cdk4 therefore inhibiting the G0/G1 transition (Soni, R., Muller, L., et al. (2000). *Biochem Biophys Res Comm,* 275(3): 877-884).

Brefeldin A—which induces cell cycle arrest in the G0/G1 phase (Nojiri, H., Manya, H., et al. (1999) *FEBS Lett,* 453(1-2): 140-144).

In a second aspect the invention is relates to use of at least one substance which is an inhibitor of progression of the cell cycle through the G1/S transition point for the manufacture of a medicament for the treatment or prevention of Alzheimer's disease.

The invention is also directed to a method of treating or preventing Alzheimer's disease in a human patient comprising administering to a human patient in need thereof an effective amount of an inhibitor of progression of the cell cycle through the G1/S transition point.

Inhibitors of progression of the cell cycle through the G1/S transition point may act via various mechanisms. For example, they may block cell cycle progression in G1, induce cell cycle arrest in G1, induce cell cycle arrest at the G1/S checkpoint via various pathways, block the G1/S transition, or inhibit DNA synthesis.

Preferably the inhibitor of progression of the cell cycle through the G1/S transition point will be a substance that, when assessed using the in vitro assay described herein, produces significant correction of the cell cycle regulatory defect at the G1/S transition in an Alzheimer's patient, most preferably the Alzheimer's patient which it is intended to treat using the substance.

Preferred known inhibitors of progression of the cell cycle through the G1/S transition point, which may be used in accordance with this aspect of the invention, include the following, however this is not to be construed as limiting the invention to these specific embodiments:

Squamocin—an annonaceous acetogenin which blocks cell cycle progression in the G1 phase (Raynaud, S., Nemati, F., et al. (1999) *Life Science,* 65(5): 525-533).

Peptide aptamers that functionally antagonize E2F activity—suitable peptide aptamers are those described and shown to be inhibitors of the cell cycle in G1 by Fabbrizio, E., Le Cam, L., et al. (1999) *Oncogene,* 18(30): 4357-4363.

Manumycin A—shown to cause G1 arrest (Wang, W. and Macaulay, R. J. (1999) *Int J Cancer,* 82(3): 430-434).

Indole carbazole K252a—a compound shown to cause cell cycle arrest at the G1/S checkpoint via p21 (Chin, L. S., Murray, S. F., et al. (1999) *Cancer Invest.*, 17(6): 391-395).

Oncostatin M and interleukin 6 in combination—this combination of cytokines induces cell cycle arrest at G1/S via p27 (Klausen, P., Pedersen, L., et al. (2000) *Oncogene*, 19(32): 3675-3683).

4-sodium phenylbutyrate—an agent that has been used for many years in the treatment of urea cycle defects, which has been shown to cause cell cycle arrest in G1 via p21 (McGrath-Morrow, S. A. and Stahl, J. L. (2000) *J Pharmacol Exp Ther*, 294(3): 941-947).

Retinoids and retinoid receptor selective ligands (e.g. ligands which mimic the effect of retinoic acid binding to the retinoid receptor, for example Targretin)—suitable retinoids include retinoic acid, which has been shown to mediate cell cycle arrest in G1 (Hsu, S. L., Hsu, J. W. et al. (2000) *Exp Cell Res*, 258(2): 322-331).

Ansamycins—members of the ansamycin class of antibiotics have been shown to inhibit the growth of human tumor cell lines in vitro. Suitable ansamycins include thiazinotrienomycin B (TT-B), shown to inhibit cell cycle progression from G0/G1 to S (Hosokawa, N., Yamamoto, S., et al. (1999) *J. Antibiot*, 52(5): 485-490; Hosokawa, N., Naganawa, H., et al. (2000) *J. Antibiot*, 53(9): 886-894), and related compounds such as, for example, herbimycin and geldanamycin.

Vitamin D analogs—suitable analogs include, but are not limited to, the compounds EB1089 and CB1093, which have been shown to cause cell cycle arrest in the G0/G1 phase (Pettersson, F., Colston, K. W., et al. (2000) *Br J Cancer*, 83(2): 239-245).

Glucocorticoids—suitable glucocorticoids include, but are not limited to, the synthetic glucocorticoid dexamethasone, which has been shown to induce cell cycle arrest in G1 via p27 and p57 (Samuelsson, M. K., Pazirandeh, A., et al. (1999) *Mol Endocrinol*, 13(11): 1811-1822).

Alpha adrenergic receptor antagonists—suitable examples include the alpha1-adrenergic receptor antagonist doxazosin, which has been shown to induce cell cycle arrest in G1 via p27 (Kintsher, U., Kon, D., et al. (2001) *J Cardiovasc Pharmacol*, 37(5): 532-539; Kintsher, U., Wakino, S., et al. (2000) *Arterioscler Thromb Vasc Biol*, 20(5): 1216-1224).

Iron chelators—suitable examples include EDTA, dexrazoxane, the synthetic iron chelator O-Trensox and desferrioxamine, both of which have been shown to block the G1/S transition (Rakba, N., Loyer, P., et al. (2000) *Carcinogenesis*, 21(5): 943-951) and also aroylhydrazone iron chelators of the pyridoxal isonicotinoyl hydrazone class, such as those shown by Becker, E. and Richardson, D. R. (1999) *J Lab Clin Med*, 134(5): 510-521 to be mediators of cell cycle arrest at G1/S.

Angiotensin II receptor antagonists—suitable examples include bradykinin, which is known to inhibit DNA synthesis (Patel, K. V. and Schrey, M. P. (1992) *Cancer Res*, 52(2): 334-340).

Immunosuppressive chemotherapeutic drugs—suitable examples are Doxorubicin, Adriamycin, Rapamycin, Cyclosporin A, FK506 (Tacrolimus) and compounds of the prodigiosin family. These immunosuppressive drugs are all known to promote G1 inhibition via p21 and p27.

Melatonin—which is known to induce G1/S inhibition (Urata, Y., Honma, S., et al. (1999) *Free Radic Biol Med*, 27(7-8): 838-847).

The above agents may also be used in combination in order to achieve the desired therapeutic effect. Certain combinations of agents may act co-operatively, additively or synergistically, when co-administered or when administered sequentially. A preferred combination is doxorubicin with rapamycin. Most preferably the two agents are administered sequentially, rapamycin followed by doxorubicin. As illustrated in the accompanying Examples, a combined treatment with rapamycin and doxorubicin has a strong protective effect against the accumulation of AD-related proteins. A further preferred combination is dexrazoxane with doxorubicin. Again the two agents are most preferably administered sequentially, dexrazoxone followed by doxorubicin. As illustrated in the accompanying Examples, treatment with dexrazoxane followed by doxorubicin enhances protection against AD-related protein expression.

The invention is also directed to the use of pharmaceutically acceptable salts of the agents listed above, and to derivatives of the listed agents which retain the desired activity of inhibiting cell cycle re-entry and progression to the G1/S transition point, or inhibiting cell cycle progression at the G1/S transition point. Derivatives that substantially retain the same activity as the starting material, or more preferably exhibit improved activity, may be produced according to standard principles of medicinal chemistry, which are well known in the art. Such derivatives may exhibit a lesser degree of activity than the starting material, so long as they retain sufficient activity to be therapeutically effective. Derivatives may exhibit improvements in other properties that are desirable in pharmaceutical active agents such as, for example, improved solubility, reduced toxicity, enhanced uptake into the brain, etc.

The above-listed agents, or pharmaceutically acceptable salts or derivatives thereof, may be formulated into pharmaceutical dosage forms, together with suitable pharmaceutically acceptable carriers, such as diluents, fillers, salts, buffers, stabilizers, solubilizers, etc. The dosage form may contain other pharmaceutically acceptable excipients for modifying conditions such as pH, osmolarity, taste, viscosity, sterility, lipophilicity, solubility etc.

Suitable dosage forms include solid dosage forms, for example, tablets, capsules, powders, dispersible granules, cachets and suppositories, including sustained release and delayed release formulations. Powders and tablets will generally comprise from about 5% to about 70% active ingredient. Suitable solid carriers and excipients are generally known in the art and include, e.g. magnesium carbonate, magnesium stearate, talc, sugar, lactose, etc. Tablets, powders, cachets and capsules are all suitable dosage forms for oral administration.

Liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Suitable diluents and solvents include sterile water, Ringer's solution and isotonic sodium chloride solution, etc. Liquid dosage forms also include solutions or sprays for intranasal administration.

Aerosol preparations suitable for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations may be conveniently prepared in unit dosage form, according to standard procedures of pharmaceutical formulation. The quantity of active compound per unit dose may be varied according to the nature of the active compound and the intended dosage regime. Generally this will be within the range 0.1 mg to 1000 mg.

Other delivery systems can include time-release, delayed release or sustained release delivery systems. Such systems can avoid repeated administrations of the therapeutic agents of the invention described herein, increasing convenience to the subject and the physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the therapeutic agent(s) of the invention are contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions such as Alzheimer's disease. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the invention involves co-administration of at least two different types of therapeutic agent for treating Alzheimer's disease. Thus, the invention provides methods and products for combination therapy in which a first therapeutic agent (e.g., an inhibitor of cell cycle re-entry and progression to the G1/S transition or an inhibitor of progression of the cell cycle through the G1/S transition point) is administered to the subject in combination with a second therapeutic agent for treating Alzheimer's disease. The second therapeutic agent can be one or more agents, which can be administered concurrently or sequentially with the first therapeutic agent. Sequential administration includes administration of the second therapeutic agent before or after the first therapeutic agent.

The second therapeutic agent in the combination can be one of the cell cycle therapeutic agents described herein, i.e., an inhibitor of cell cycle re-entry and progression to the G1/S transition or an inhibitor of progression of the cell cycle through the G1/S transition point. The second therapeutic agent may also be non-cell cycle therapeutic agent for treating Alzheimer's disease, such as agents that reduce the effects of neuron loss in the central nervous system (e.g., acetylcholine esterase inhibitors, such as donepezil, rivastigmine and galantamine) and agents that reduce the amount of or stop the deposition of beta-amyloid plaques in the brain (e.g., beta- and gamma-secretase inhibitors, Abeta vaccination, Cu—Zn chelators, cholesterol-lowering drugs and non-steroidal anti-inflammatory drugs).

The present invention also includes pharmaceutical kits useful for the treatment of Alzheimer's disease. The kits comprise one or more containers containing a pharmaceutical composition comprising a therapeutically effective amount of one or more therapeutic agents of the present invention or a salt or a prodrug thereof. The kits include one or more cell cycle therapeutic agents as described herein, and may include one or more second therapeutic agents, including a cell cycle therapeutic agent and/or another type of therapeutic for treating Alzheimer's disease, as described above. Such kits can further include, if desired, one or more of various conventional pharmaceutical kit components, such as, for example, containers with one or more pharmaceutically acceptable carriers, additional containers, etc., as will be readily apparent to those skilled in the art. Instructions, such as printed instructions either as inserts or as labels or the like, the instruction indicating quantities of the components to be administered in accordance with the present invention, guidelines for administration, and/or guidelines for mixing the components, can also be included with the kit.

"Treating" or "treatment" as used herein with reference to Alzheimer's disease describes the management or care of a patient for the purposes of combatting the disease, and includes the administration of the active agent to reduce or prevent the onset or severity of the symptoms or complications, i.e. prophylaxis. The term "Alzheimer's disease patient" encompasses individuals at all stages of disease, including asymptomatic individuals who do not manifest clinical signs of AD, but have been diagnosed as carrying an abnormality that would be expected to lead to the development of clinical symptoms in the absence of preventative/prophylactic treatment. This includes individuals diagnosed as carrying a cell cycle regulatory defect at the G1/S transition and individuals identified as carrying mutations/genetic variations of the cell cycle regulatory and/or DNA repair genes associated with the development of sporadic AD.

The active agents are to be administered to human subjects in "therapeutically effective amounts", which is taken to mean a dosage sufficient to provide a medically desirable result in the patient. In Alzheimer's disease, an effective amount is an amount that provides significant correction of the cell cycle regulatory defect G1/S transition within neurons of the patient. The exact dosage and frequency of administration of a therapeutically effective amount of active agent will vary, depending on such factors as the nature of the active substance, the dosage form and route of administration. The appropriate dosage regime for a given patient will generally be determined by a medical practitioner having regard to such factors as the severity of disease, and the age, weight and general physical condition of the patient, and the intended duration of treatment as would be appreciated by those skilled in the art.

In Alzheimer's disease it is envisaged that treatment will be administered continuously over a long period of time to prevent or slow the development of AD-type pathology in the brain. Oral dosage forms are particularly preferred for long term therapy and prophylactic treatment because of convenience for the patient.

Many of the preferred agents listed above are cell cycle regulatory drugs which have previously been known for use as antineoplastic/chemotherapeutic agents in the treatment of cancer. For use as antineoplastics, such agents are generally administered in very high doses over a limited period of time, having regard to their long-term cytotoxicity. In the treatment of Alzheimer's disease, such agents will generally be administered at a very much lower dosage, since it is desired to selectively reverse cell cycle regulatory defects in the neurons and not other actively dividing cells. Thus the therapeutic agents will preferable by used (and packaged in kits, if so desired) in the present invention in amounts that are not effective for use as antineoplastic/chemotherapeutic agents. Use may be made of delayed, slow or sustained release formulations or formulations specifically targeted to the brain in order to achieve the correct dosage.

In Vitro Screens to Identify Compounds which Affect the G1/S Transition

In order to identify compounds which have an effect on regulation of the G1/S transition and therefore have potential utility in the treatment of Alzheimer's disease, a simple in vitro screen may be performed using cultured cells which exhibit a cell cycle regulatory defect at the G1/S phase transition. The cells are exposed to a sample of the compound then the effect of the compound on cell cycle regulation at G1/S is analyzed. Compounds that correct the cell cycle regulatory defect at the G1/S transition are scored as having potential pharmacological activity in the treatment of Alzheimer's disease.

The screen may be performed using essentially any cells that exhibit an analogous cell cycle regulatory defect at the G1/S phase transition to that observed in the neurons in Alzheimer's disease. Suitable cells may include cultured lymphocytes derived from an individual, or several individuals, having Alzheimer's disease. Thus, the same methodology may be used as the basis of a compound screen to identify agents having potential utility in the treatment of Alzheimer's disease; or it may be used to test agents which are known to have potential utility in the treatment of Alzheimer's against cells taken from a particular Alzheimer's patient in order to identify the agent(s) which is/are most likely be effective in that particular patient. As discussed previously, different patients will respond to treatment with different agents, depending on the precise nature of the defect underlying abnormal cell cycle regulation in that patient.

Methods for testing whether a cell exhibits a regulatory defect at the G1/S phase transition are described in the accompanying Examples. Similar methodology is used as the basis of the screening method in order to analyze the regulation of the G1/S transition in the presence and absence of candidate compounds.

Cells exhibiting a regulatory defect at the G1/S transition are exposed to candidate compounds and the effect of the candidate compound on regulation of the G1/S transition is assessed with reference to suitable controls, e.g. cells not exposed to any test compound. In a typical screen the candidate compound will be tested at a range of different concentrations, including a zero concentration control. Compounds that restore "normal" regulation at the G1/S transition are potentially useful in the treatment of Alzheimer's disease. This method may be used to establish whether compounds which are known inhibitors of cell-cycle re-entry and progression to the G1/S transition or known inhibitors of progression of the cell cycle through the G1/S transition point from other experimental systems are effective in cells which model the defect present in Alzheimer's disease.

The basic screening methodology may also be adapted for use in assessing the efficacy of a form of treatment for Alzheimer's disease, for example to test the effect of a particular pharmacological agent on cell cycle regulation.

In a useful variation, the method may be used specifically to determine whether a given pharmacological agent is likely to be of benefit in the treatment of Alzheimer's disease in a particular human individual. In this case the assay is performed using non-neuronal cells from the individual that exhibit a cell cycle regulatory defect at the G1/S phase transition, most preferably cultured lymphocytes. The cells are tested for the presence of the defect in regulation at the G1/S phase transition in the presence and absence of the pharmacological agent. Pharmacological agents that result in "correction" of the regulatory defect at the G1/S transition are identified as likely to be of benefit in the treatment of Alzheimer's disease in the individual. By "correction" is meant a significant degree of restoration to normal cell cycle regulation. This may be assessed by reference to control cells, for example cells of the same type taken from an age-matched control individual not having Alzheimer's disease or any evidence of a regulatory defect at the G1/S transition or any genetic defect/allelic variation in cell cycle regulatory genes and/or DNA repair genes which might be expected to predispose to Alzheimer's disease.

In a specific embodiment the invention provides a method of selecting a pharmaceutical agent for use in the treatment Alzheimer's disease in a human patient, which method comprises:
(a) exposing cells from the patient, which cells are non-neuronal cells that exhibit a cell cycle regulatory defect at the G1/S phase transition, to a panel of pharmaceutical agents which are known inhibitors of cell cycle re-entry and progression to the G1/S transition or known inhibitors of progression of the cell cycle through the G1/S transition point,
(b) analyzing the regulation of the G1/S transition the cells in the presence and absence of the pharmacological agents, and
(c) identifying an agent that corrects the regulatory defect at the G1/S transition in the cells, which agent is identified as likely to be of benefit in the treatment of Alzheimer's disease in the patient.

This method may be performed using essentially any non-neuronal cells that exhibit an analogous cell cycle regulatory defect at the G1/S phase transition to that observed in the neurons in Alzheimer's disease. Suitable cells may include cultured lymphocytes derived from the Alzheimer's patient under test.

"Analysis" of the regulation of the G1/S transition may be performed using any of the methods described herein as being suitable for screening compounds affecting the cell cycle regulatory defect at G1/S. Advantageously, the method used for analysis of the regulation of the G1/S phase transition will be one capable of being performed in multi-well microtiter plates, allowing multiple pharmaceutical agents and multiple concentrations to be tested in parallel in mid-to-high throughput format. The most preferred method suitable for use in a mid-to-high throughput format is the cell proliferation assay.

In a further aspect the invention relates to a method of screening compounds for potential pharmacological activity in the treatment of Alzheimer's disease, which method comprises:
contacting SH-SY5Y neuroblastoma cells with candidate compounds and testing for at least one parameter indicative of Alzheimer's disease pathology selected from:
(i) Cell survival and proliferation
(ii) Apoptosis
(iii) Relative lengthening of the G1 phase of the cell cycle
(iv) Relative lengthening of the G2 phase of the cell cycle
(v) Expression of amyloid precursor protein (APP)

(vi) Expression of AD-type hyperphosphorylated tau protein
(vii) Expression of AD-type PHF tau protein wherein candidate compounds which cause a reduction in the tested parameter(s), as compared to control cells not exposed to the candidate compound, are scored as having potential pharmacological activity in the treatment of Alzheimer's disease.

SH-SY5Y cells provide an in vitro model of AD pathology, which may be used to identify compounds which have a significant effect in reducing AD pathology, and are therefore useful in the treatment of Alzheimer's disease. The skilled reader will appreciate that equivalent screens may be carried out using cells other than SH-SY5Y cells, particularly other neuroblastoma cells, which exhibit similar characteristics, for example expression of APP and hyperphosphorylated tau. Preferred features of the assay are described in the accompanying Examples.

There is no limitation on the types of candidate compounds to be tested in the screening methods of the invention. The method may be used to test essentially any compound that it is desired to screen in order to determine its effects on AD pathology. Candidate compounds may include compounds having a known pharmacological or biochemical activity, compounds having no such identified activity and completely new molecules or libraries of molecules, such as might be generated by combinatorial chemistry.

In a preferred application, the method may be used to test known inhibitors of cell cycle re-entry and progression to the G1/S transition and known inhibitors of progression of the cell cycle through the G1/S transition point in a model of AD in order to confirm utility in the treatment of Alzheimer's.

The invention will be further understood with reference to the following experimental examples, together with the accompanying Figures.

EXAMPLES

Example 1

Procedures Used to Test for the Presence of a Cell Cycle Regulatory Defect at the G1/S Transition The following methods of testing for the presence of a cell cycle regulatory defect at the G1/S transition may be used "diagnostically" in order to test whether a given cell exhibits the regulatory defect and may also form the basis of compound screening methods. For compound screening applications, candidate compounds may be added before the cells are treated to induce cell division and elicit cell cycle arrest.

Method (A): (i) Induce the cells to divide (e.g., by the addition of a mitogenic stimulus, for example one or more growth factors), then (ii) elicit cell cycle arrest by addition of a cell division inhibitor substance (most preferably a specific G1 inhibitor, for example rapamycin), and (iii) test the responsiveness of the cells' G1/S cell cycle regulatory mechanisms to the addition of the cell division inhibitor substance, in the presence or the absence of a candidate compound.

or

Method (B): (i) Induce the cells to divide (e.g., by the addition of a mitogenic stimulus, for example one or more growth factors), then (ii) expose the cells to a stimulus which induces cell cycle arrest at G1 (e.g. ionising radiation, hypoxia, UV radiation, etc), and (iii) test the responsiveness of the G1/S cell cycle regulatory mechanisms of the cells to the addition of the stimulus which elicits cell cycle arrest, in the presence or the absence of a candidate compound.

The rationale behind both (A) and (B) is to first stimulate the cells to divide, then attempt to arrest the cell cycle at the G1 stage using either a cell division inhibitor (method (A)) or other stimulus eliciting cell cycle arrest (method (B)) and then evaluate the effect of such treatment on the cell cycle regulatory system. The effect on cell cycle regulation may be evaluated by a variety of different means, as discussed below. The treatment with a cell division inhibitor (method (A)) or other stimulus that induces cell cycle arrest (method (B)) is referred to herein as "cell cycle inhibitory treatment" or "inhibitory treatment". If a cell cycle regulatory defect at the G1/S transition is present, then this will affect the responsiveness of the cells to attempted cell cycle arrest. In general, the presence of a cell cycle regulatory defect at G1/S results in a reduced responsiveness to "inhibitory treatment" with a cell division inhibitor or other stimulus that induces cell cycle arrest at G1, i.e., the inhibitory treatment is less effective in arresting the cell cycle at the G1/S checkpoint in cells with such a defect.

Various approaches may be implemented before and after the addition of the mitogenic stimulus to induce cell division, or before and after the attempted arrest of the cell cycle, to test the responsiveness of the cells to cell cycle inhibitory treatment. Preferred approaches are listed below by way of example:

(1) Proliferation Assay Performed in Order to Assess Whether Cell Cycle Arrest has Occurred and to what Extent as a Result of Inhibitory Treatment.

The proliferation assay may be carried out according to any of the standard protocols known in the art. A particularly suitable example is the MTT survival assay (commercially available from Chemicon International Ltd, see Mosmann, T. In *J. Immunol. Methods,* 1983, vol: 65, 55-63).

In a typical screen, proliferation assays are performed on both cells treated with a cell division inhibitor (method (A)) or other stimulus inducing cell cycle arrest (method (B)) and untreated control cells from the same subject, in the presence of varying concentrations of the candidate compound. Since the inhibitory treatment (using method (A) or (B)) will be effective only in the presence of an intact G1/S regulatory system, the difference in degree of proliferation between the treated and untreated cells will be significantly smaller in Alzheimer's disease patients (who lack effective regulation at G1/S) than in age-matched control individuals. In general, little or no change in the proliferative activity of cells from the subject in the presence of inhibitory treatment indicates a reduced responsiveness to cell cycle inhibition in the G1 phase, and hence the presence of a regulatory defect at the G1/S transition. Candidate compounds which cause a reduction of proliferative activity in cells from a particular Alzheimer's patient in the presence of inhibitory treatment are scored as potentially useful in the treatment of Alzheimer's disease in that patient, because they are able to prevent progression through the cell cycle in cells of the Alzheimer's patient. Such screens also are useful in diagnosis of Alzheimer's disease in subjects that are suspected of having AD (with some or no clinical manefestations of the disease), or who have a genetic predisposition to AD.

(2) Calculating the Relative Lengthening of the G1 Phase of the Cell Cycle in Cells from the Subject as a Result of Exposure to a Cell Division Inhibitor or Stimulus that Induces Cell Cycle Arrest.

The relative lengthening (RL) of the G1 phase as a result of exposure to a cell division inhibitor (method (A)) or stimulus that induces cell cycle arrest (method (B)) is calculated using the formula RL=100f−100 (expressed as a percent). "f" is the ratio of the time in G1 for cells (non-neuronal cells from the subject under test) exposed to inhibitory treatment with the cell division inhibitor or stimulus that induces cell cycle arrest ($TG1_{tr}$) versus the time in G1 for untreated control cells (i.e. also non-neuronal cells from the subject under test) not exposed to inhibitory treatment ($TG1_c$). f may be calculated according to the following relation:

$$f = TG1_{tr}/TG1_c = [\ln 2 - \ln(2-G1_{tr})][\ln(2-G1_c)]/[\ln(2-G1_{tr})][\ln 2 - \ln(2-G1_c)]$$

(Darzynkiewicz, Z. (1993) In Fantes P and Brooks R (eds) *The cell cycle*. Oxford University Press, Oxford, pp 43-68).

Various techniques may be employed to obtain the values of $TG1_{tr}$ and $TG1_c$. In a preferred embodiment $TG1_{tr}$ and $TG1_c$ may be obtained by determining the proportion of cells in the various phases of the cell cycle for both treated cells (non-neuronal cells from the test subject treated with the cell division inhibitor substance or stimulus that induces cell cycle arrest) and untreated control cells (non-neuronal cells from the same subject not exposed to the cell division inhibitor substance or stimulus that induces cell cycle arrest), in the presence of varying concentrations of candidate compound. The proportion of cells in the various phases of the cell cycle may be readily determined by incorporation of a labelled nucleotide analogue, preferably bromodeoxyuridine (BrdU), followed by fluorescence activated cell sorting (FACS analysis), or equivalent, as described in detail in Example 2.

The presence of a cell cycle regulatory defect at the G1/S phase transition is indicated by a reduced relative lengthening of the G1 phase in the presence of the cell division inhibitor substance or stimulus in cells from the Alzheimer's subject, as compared to control cells not having a cell cycle regulatory defect at the G1/S phase transition (e.g. cells of the same type taken from an age-matched control individual not having Alzheimer's disease or any evidence of a regulatory defect at the G1/S transition or any genetic defect/allelic variation which might be expected to pre-dispose to Alzheimer's disease). The control cells not having a cell cycle regulatory defect at the G1/S phase transition are not to be confused with the "untreated control" cells used for calculation of RL, which are cells from the test subject which have not been exposed to inhibitory treatment.

Candidate compounds which cause an increase in relative lengthening of the G1 phase in cells from a particular Alzheimer's patient in the presence of inhibitory treatment are scored as potentially useful in the treatment of Alzheimer's disease in that patient, because they are able to prevent progression through the cell cycle in cells of the Alzheimer's patient.

(3) Assessment of Cell Cycle Regulatory Protein or mRNA Expression.

Expression of cell cycle regulatory proteins may be assessed using standard techniques well known in the art such as, for example, immunoblotting, western blotting, ELISA or related methods. Assessment of expression of corresponding mRNAs encoding the cell cycle regulatory proteins may also be accomplished by means of standard methods such as, for example, hybridization techniques, "DNA chip" analysis or related methods or amplification-based techniques such as reversed transcription (RT)-PCR, real time-PCR, nucleic acid sequence-based amplification (NASBA), etc. Suitable methods for the detection/quantitation of mRNAs that may be used in accordance with the invention will be well known to those skilled in the art. Certain of these methods, for example RT-PCR, rely on detection/quantitation of a cDNA copy of the relevant mRNA.

The cell cycle regulatory defect present in Alzheimer's disease may result in changes in the pattern of expression of cell cycle regulatory proteins, and their corresponding mRNAs. Screening for changes in expression of particular cell cycle regulatory proteins and/or the corresponding mRNAs may therefore be used diagnostically to identify the presence of a cell cycle regulatory defect at G1/S. In addition, expression of cell cycle regulatory proteins may be used as a marker of progression through the cell cycle. Hence, the responsiveness of cells to inhibitory treatment (using method (A) or method (B), described above) may be assessed by looking at the expression of one or more cell cycle regulatory proteins, in order to determine the extent to which inhibitory treatment causes cell cycle arrest in cells from the test subject. Suitable cell cycle regulatory proteins include, but are not limited to, CDKN3, p15ink4B, p16ink4A, p19ink4D, p27kip1, p21cip1, p57kip2 and TP53. Full cDNA and amino acid sequences for these proteins are publicly available: a list of OMIM accession numbers for these proteins is provided below. OMIM is Online Mendelian Inheritance in Man, a database which is a catalog of human genes and genetic disorders. OMIM is accessible via the website of the National Center for Biotechnology Information (NCBI). Antibodies useful in the detection of each of these proteins are available commercially, or may be prepared according to standard techniques known in the art.

Candidate compounds which cause the mRNA and/or protein expression profile for cell cycle regulatory proteins in cells from a particular Alzheimer's patient to resemble that of a "normal" cell with intact regulation at the G1/S transition, are scored as being potentially useful in the treatment of Alzheimer's disease in that patient, because they are able to prevent progression through the cell cycle in cells of the Alzheimer's patient.

(4) Assessment of Cell Viability and Cell Death by any Method Known in the Art.

When a proliferating cell is arrested in the G1/S transition one of two possible "downstream" phenomena may result, either differentiation or programmed cell death. These downstream phenomena may be used as an indication of the presence in a cell population of a regulatory defect at the G1/S transition, since if regulation of the G1/S transition is defective then the downstream effects of cell cycle arrest at G1/S will also be abnormal. A lower degree of cell death or higher degree of cell viability in response to inhibitory treatment (using method (A) or method (B)) in cells from a test subject, as compared to control cells, is taken as an indication that the subject has Alzheimer's disease.

Candidate compounds which cause a higher degree of cell death or lower degree of cell viability in response to inhibitory treatment (using method (A) or method (B)) in cells from a particular Alzheimer's patient are scored as being potentially useful in the treatment of Alzheimer's disease in that patient.

(5) Assessment of Cell Death Related (Inducing or Preventing) Protein or mRNA Expression Using Standard Techniques Known in the Art.

In this approach, expression of cell death related proteins, or the corresponding mRNAs, is used as an indirect assessment of the downstream effects of inhibitory treatment with a cell division inhibitor (method (A)) or a stimulus inducing cell cycle arrest at the G1/S transition (method (B)). Suitable cell death related proteins include, for example, members of the bcl-2 family of proteins, of which there are many known in the art. Monoclonal antibody to Bcl-2 is commercially available from Sigma Corp. (St. Louis, Mo.), or may be prepared according to standard techniques known in the art.

Candidate compounds which cause the mRNA and/or protein expression profile for cell death-related proteins in cells from a particular Alzheimer's patient to resemble that of a "normal" cell with intact regulation at the G1/S transition, are scored as being potentially useful in the treatment of Alzheimer's disease in that patient.

(6) Assessment of the Expression of DNA Damage Response Element Proteins or Corresponding mRNAs Using Standard Techniques.

This approach may be used when the stimulus used to induce cell cycle arrest at G1/S is DNA damage, for example treatment with a chemical agent which causes DNA damage or exposure to UV radiation. Under normal circumstances the presence of DNA damage will induce a cell to arrest at the G1/S phase transition and attempt to repair the damaged DNA via activation of DNA damage response pathways. Alterations in the pattern of expression of proteins involved in the normal response to DNA damage, or the corresponding mRNAs, in response to the presence of damaged DNA may therefore be used as an indication of the presence of a cell cycle regulatory defect at the G1/S phase transition. Suitable DNA damage response elements include (OMIM accession numbers in parentheses), for example, TP53, Gadd34, Gadd45A(126335), Gadd45B(604948), Gadd45G(604949), Gadd153(126337) and PCNA(176740). A list of OMIM accession numbers for these DNA damage response elements is provided below. Antibodies specific for these proteins are available, or may be prepared according to standard techniques known in the art.

Candidate compounds which cause the mRNA and/or protein expression profile for DNA damage response elements in cells from a particular Alzheimer's patient to resemble that of a "normal" cell with intact regulation at the G1/S transition, are scored as being potentially useful in the treatment of Alzheimer's disease in that patient.

(7) Assessment of the DNA Content of the Non-Neuronal Cells, with or without Cell Cycle Analysis.

In this approach, measurement of the DNA content of cells from the test subject treated with a cell division inhibitor (method (A)) or other stimulus inducing cell cycle arrest (method (B)) provides an indirect indication of the presence of a regulatory defect at the G1/S transition in such cells. The rationale behind this method is the difference in DNA content between cells in the G1 phase and cells in the G2 phase that have passed through the DNA replication stage of the cell cycle. When a population of normal cells (i.e. without a regulatory defect at G1/S) are treated to induce cell cycle arrest in G1 or at G1/S, the majority of the cells will remain in the G1 phase. However, if cells have a regulatory defect at G1/S, a proportion of the cells will pass through the G1/S checkpoint and undergo DNA replication. Thus an increased DNA content in cells from a test subject, as compared to control cells not having a regulatory defect at G1/S, following treatment to induce cell cycle arrest at G1 is taken as an indication of the presence of a regulatory defect at G1/S.

Candidate compounds which cause decreased DNA content in cells from a particular Alzheimer's patient exposed to inhibitory treatment (as compared to control cells exposed to no or zero control candidate compound), are scored as being potentially useful in the treatment of Alzheimer's disease in that patient, because they are able to prevent progression through the cell cycle in cells of the Alzheimer's patient.

Online Mendelian Inheritance in Man (OMIM) Accession Numbers for Exemplary Cell Cycle Regulatory Proteins and DNA Damage Response Elements:

| Gene/protein | OMIM Accession number |
|---|---|
| CDKN3 | 123832 |
| p15ink4B | 600431 |
| p16ink4A | 600160 |
| p19ink4D | 600927 |
| p27kip1 | 600778 |
| p21cip1 | 116899 |
| p57kip2 | 600856 |
| TP53 | 191170 |
| Gadd45A | 126335 |
| Gadd45B | 604948 |
| Gadd45G | 604949 |
| Gadd153 | 126337 |
| PCNA | 176740 |
| Ku70 | 152690 |
| KU80 | 194364 |
| Ku86 | 604611 |
| NDHII | 603115 |
| BLM | 604610 |
| RECQL | 600537 |
| RECQL4 | 603780 |
| RECQL5 | 603781 |

Key references for these proteins are as follows:

CDKN3: Cyclin-dependent kinase inhibitor 3, also known as cyclin-dependent kinase interactor 1 (CDI1), Gyuris, J. et al. *Cell* 75: 791-803, 1993; Hannon, G. J. et al. *Proc Natl Acad Sci USA* 91: 1731-1735, 1994.

p15ink4B: cyclin dependent kinase inhibitor 2B, also known as CDKN2B, MTS2, TP15, Hannon, G. J. and Beach, D. *Nature* 371: 257-261, 1994; Quelle, D. E. et al. *Oncogene* 11: 635-645, 1995; Stone, S. et al. *Oncogene* 11: 987-991, 1995. Antibody to P15 is commercially available from BD Biosciences Clontech.

p16ink4A: cyclin dependent kinase inhibitor 2A, also known as CDKN2A, MTS1, TP16, Quelle, D. E. et al. *Oncogene* 11: 635-645, 1995; Kamb, A. et al. *Science* 264: 436-440, 1994; Kamb, A. et al. *Nature Genetics* 8: 22-26, 1994. Monoclonal antibody to p16ink4A is commercially available from Sigma Corp.

p19ink4D: cyclin-dependent kinase inhibitor 2D, also known as CDKN2D, Hirai, H. et al. *Mol Cell Biol* 15: 2672-2681, 1995; Okuda, T. et al. *Genomics* 29: 623-630, 1995. Antibody to p19 is commercially available from BD Biosciences Clontech.

TP53: tumour protein p53, or p53, Levine, A. J. et al. *Nature* 351: 453-456, 1991; Levine, A. J. *Cell* 88: 323-331, 1997. Monoclonal antibody to TP53 is commercially available from Sigma Corp.

p27kip1: cyclin dependent kinase inhibitor 1B, also known as CDKN1B, KIP1, Toyoshima, H. and Hunter, T. *Cell* 78: 67-74, 1994. Antibodies to p27 are commercially available from BD Biosciences Clontech and Sigma Corp.

p21cip1: cyclin dependent kinase inhibitor 1A, also known as CDKN1A, WAF1, Harper, J. W. et al. *Cell* 75: 805-816, 1993. Antibody to p21cip1 is commercially available from BD Biosciences Clontech.

p57kip2: cyclin dependent kinase inhibitor 1c, also known as CDKN1C, KIP2, Lee, M-H. et al. *Genes Dev* 9: 639-649, 1995.

Gadd45A: growth arrest and DNA damage inducible gene alpha, also known as DDIT1, Carrier, F. et al. *J Biol Chem* 269: 32672-32677, 1994; Kearsey, J. M. et al. *Oncogene* 11: 1675-1683, 1995; Smith, M. L. et al. *Science* 266: 1376-1380, 1994.

Gadd45B: growth arrest and DNA damage inducible gene beta, De Smeale, E. et al. *Nature* 414: 308-313, 2001.

Gadd45C: growth arrest and DNA damage inducible gene gamma, Takekawa, M. and Saito, H. *Cell* 95: 521-530, 1998.

Gadd153: DNA damage inducible-transcript, also known as CHOP, Ron, D. and Habener, J. F. *Genes Dev* 6: 439-453, 1992; Park, J. S. et al. *Gene* 116: 259-267, 1992.

PCNA: proliferating cell nuclear antigen, Travali, S. et al. *J Biol Chem* 264: 7466-7472, 1989. Antibody to PCNA is commercially available from Sigma Corp.

Ku70: thyroid autoantigen, also known as G22P1, p70, TLAA, Chan, J. Y. C. et al. *J Biol Chem* 264: 3651-3654, 1989.

Ku80: X-ray repair, complementing defective, in chinese hamster, 5, also known as XRCC5.

Ku86: Cooper, M. P. et al. *Genes Dev* 14: 907-912, 2000.

NDHII: DEAD/H BOX 9 protein, also known as DDX9, RNA helicase A, nuclear DNA helicase II, Lee, C. G. and Hurwitz, J. *J Biol Chem* 268: 16822-16830 1992; Zhang, S. and Grosse, F. *J Biol Chem* 272: 11487-11494, 1993.

BLM: Bloom syndrome gene, also known as RECQ protein-like 3, RECQL3, RECQ2, Ellis, N. A. et al. *Cell* 83: 655-666, 1995.

RECQL: RECQ protein-like, also known as RECQL1, Puranam, K. L. and Blackshear, P. J. *J Biol Chem* 269: 29838-29845, 1994; Puranam, K. L. et al. *Genomics* 26: 595-598, 1995.

RECQL4: RECQ protein-like 4, also known as RECQ4, Kitao, S. et al. *Genomics* 443-452, 1998.

RECQL5: RECQ protein-like 5, also known as RECQ5, Kitao, S. et al. *Genomics* 443-452, 1998.

Example 2

Protocols for Diagnostic Tests

The following are specific protocols for separation and culture of lymphocytes, induction of cell division, induction of cell cycle arrest by either treatment with a cell division inhibitor or $H_2O_2$-induced hypoxia, BrdU incorporation/FACS analysis and MTT survival assay. These protocols, or minor adaptations thereof, may all be used diagnostically to test for the presence of a regulatory defect at the G1/S transition and in compound screening assays.

Lymphocyte Separation

Blood is collected in lithium heparin or EDTA vacutainers. Lymphocytes are isolated according to a standard protocol using Ficoll (Sigma). In order to standardize the culture methods for all patients, the separated lymphocytes are frozen and stored for further analysis.

When lymphocytes are needed for culture, they are thawed in a 37° C. water bath and washed twice in RPMI (any medium or buffer which supports lymphocyte survival may be used to wash the cells with equivalent effect). Cell viability (e.g., by Trypan Blue exclusion) is typically approximately 80-90%.

Lymphocyte Culture, Induction of Cell Division, Induction of Cell Cycle Arrest with Cell-Cycle Inhibitor, BrdU Incorporation and FACS Analysis Lymphocyte cultures are set up in duplicate in RPMI medium supplemented with 10% FCS at a concentration of $1 \times 10^6$ cells per 1 ml of culture media. Phytohaemaglutinin (PHA) is added to the cultures at a final concentration of 22 µg/ml to activate the lymphocytes. Cultures are incubated for 48 hours at 37° C. in a humidified atmosphere containing 5% $CO_2$. After 48 hours incubation one culture is treated with 100 ng/ml rapamycin, while the other untreated culture is kept as a control.

After a further 23 hours incubation BrdU is added at a concentration of 10 µg/ml to all cultures. After another hour cultures are "collected" and fixed in 70% ice-cold ethanol.

BrdU incorporation is assessed using immunohistochemistry, followed by FACS analysis. The proportion of cells in various phases of the cell cycle is determined and data transformation performed to obtain the relative lengthening of the G1 phase.

Calculations of relative lengthening of the G1 phase of the cell cycle in treated cultures relative to control cultures are based on the assumptions that cells are in the exponential phase of proliferation, and that the growth fraction in the cultures (ratio of dividing cells versus quiescent cells) is 1.0 (Darzynkiewicz Z (1993) In Fantes P and Brooks R (eds) *The cell cycle*. Oxford University Press, Oxford, pp 43-68). It is also assumed that rapamycin only alters the length of the G1 phase (Wagner E F, Hleb M, Hanna N and Sharma S (1998) *J Immunol* 161: 1123-31). Based on these assumptions, the relative lengthening of the G1 phase is calculated using the formula: RL=100f−100 (expressed in percent). The ratio of the G1 time in treated versus control cultures:

$$f = TG1_t/TG1_c = [\ln 2 - \ln(2-G1_t)][\ln(2-G1_c)]/[\ln(2-G1_t)][\ln 2 - \ln(2-G1_c)]$$ (Darzynkiewicz, Z., 1993, ibid.)

Lymphocyte Culture, Induction of Cell Division, Induction of Cell Cycle Arrest with $H_2O_2$-Induced Hypoxia, MTT Survival Assay Four sets of lymphocyte cultures are set up as above. Control cultures are left without any treatment, one set of cultures is treated with 100 ng/ml rapamycin, the third set is treated with 1 µM doxorubicin while the fourth set is treated with 120 µM $H_2O_2$. Doxorubicin induces DNA damage, leading to arrest at G2/M, rather than G1/S. $H_2O_2$ treatment produces oxidative stress, leading to a reversible and temporary cell cycle arrest at G1/S.

After 20 hours of incubation a 4 hour long MTT survival assay (Chemicon International Ltd) is set up. Results are read using a microplate reader (570 filter, 630 reference filter). The ratio between cell numbers in treated cultures versus controls is expressed as percent.

Example 3

Examining the Effects of Cell Cycle Inhibitor Drugs on Cell Division Kinetics and Alzheimer's-Type Protein Expression in the SH-SY5Y Neuroblastoma Cell Line The object of this study was to demonstrate that exemplary cell cycle inhibitor drugs are able to reduce indicators of Alzheimer's disease pathology in an in vitro model of Alzheimer's disease. There is currently no available animal model for sporadic Alzheimer's disease. However, the SH-SY5Y neuroblastoma cell line (ATCC accession number CRL-2266) is accepted as a suitable in vitro model.

SH-SY5Y cells were treated with three candidate agents: rapamycin (Rapa) at 100 ng/ml, doxorubicin (Doxo) at 1 µM and Dexrazoxane (DexRaz) at 200 µM and then tested one day (d1) and two days (d2) after treatment for the following 7 parameters, which are indicative of cell cycle defects and "AD-type" pathology:
Parameters Indicative of Changes in Cell Cycle/Cell Division Kinetics:
 1) Cell survival and proliferation
 2) Apoptosis
 3) Relative lengthening of the G1 phase of the cell cycle
 4) Relative lengthening of the G2 phase of the cell cycle
Expression of AD-Related Proteins:
 5) Expression of amyloid precursor protein (APP)
 6) Expression of AD-type hyperphosphorylated tau protein
 7) Expression of AD-type paired helical filament (PHF) tau protein
The results are shown in FIGS. 1 to 7.

In order to evaluate the effect of drug pre-treatment is protecting against the effects of oxidative stress cells were subjected to oxidative stress (by treatment with 120 μM $H_2O_2$) in the absence of drug treatment and after treatment with rapamycin or dexrazoxane, and then tested for the same parameters. Results are shown in FIGS. 1-7, panel b (FIG. 1b, FIG. 2b, FIG. 3b, FIG. 4b, FIG. 5b, FIG. 6b, FIG. 7b).

Finally, cells were treated with doxorubicin after treatment with rapamycin or dexrazoxane and then tested for the same parameters, to evaluate the effects of combined treatment. Results are shown in FIGS. 1-7, panel c (FIG. 1c, FIG. 2c, FIG. 3c, FIG. 4c, FIG. 5c, FIG. 6c, FIG. 7c).

Methods

SH-SY5Y human neuroblastoma cells were cultured in Dulbecco's modified Eagle's medium (DMEM)/F12 supplemented with 10% fetal calf serum (FCS, PAA Laboratories, Austria), 2 mM L-glutamine, 100 IU/ml penicillin and 100 μg/ml streptomycin (Gibco) in a humidified incubator at 37° C. and 5% $CO_2$.

After 24 h incubation the culture medium was replaced by DMEM/F12 with 10% FCS containing various concentrations of drug. The cells were incubated for another 24 or 48 hours.

Cell survival and proliferation was assessed by MTT proliferation and cell survival assay, performed according to the manufacturers recommendations (Chemicon International, Ltd., Hampshire, UK) in the final 4 hours of the 24 hours period. The results of the assay were evaluated using an Opsys MR ELISA plate reader (Dynex Technologies, Middlesex, UK) at 570 nm with a reference wavelength of 630 nm.

The cell cultures were repeated in identical conditions in order to analyze cell cycle kinetics by flow cytometry and to study protein expression.

The cultures prepared for flow cytometry were harvested after a short incubation with Trypsin EDTA (Sigma) in PBS. Cells were fixed in 70% ice-cold alcohol. Prior to staining with propidium iodide (PI) the samples were washed twice in PBS containing Triton-X at 0.1%. On flow cytometry the ratio of G1 and G2 cells was measured. Cells with sub-G1 DNA content were regarded as the apoptotic fraction.

The cultures prepared for protein expression assays were harvested after a short wash with cold PBS by scraping. The collected cells were lysed in 150 μl of lysis buffer containing 50 mM Tris-HCl (pH 7.4), 100 mM NaCl, 1 mM EDTA, 0.5% (v/v) Nonidet P-40, 50 mM NaF, 0.2 mM $Na_3VO_4$, 20 μg/ml phenylmethylsulfonyl fluoride, and 5 μg/ml leupeptin, and incubated on ice for 30 min. The cell lysate was centrifuged at 14,000 g for 20 min at 4° C. to remove insoluble pellets. Protein concentration was determined by the Bradford assay. ELISA assays were performed using a panel of antibodies. Secondary antibodies (anti rabbit or anti mouse as appropriate) conjugated to horseradish peroxidase were used.

Antibodies used in this study:

| Antigen | Antibody | Dilution | Source |
|---|---|---|---|
| Phosphorylated tau | AT8 | 1:1000 | Insight Biotechnology |
| PHF tau | Tau2 | 1:1000 | Novocastra |
| APP | APP | 1:1000 | Novocastra |

Results

The addition of 100 ng/ml rapamycin to the SH-SY5Y neuroblastoma culture resulted in significantly lower cell numbers in the culture than in control cultures (FIG. 1a). This cell number reduction was not due to apoptosis, since rapamycin also protected the neuroblastoma cells against apoptosis (FIG. 2a). The reduced cell numbers were due to lengthening of the cell division process, primarily the G2 phase of the cell cycle (FIG. 4a). This was associated with a small increase in APP production (FIG. 5a), and PHF-tau formation (FIG. 7a). The treatment also increased the amount of hyperphosphorylated tau after one day (FIG. 6a). The cell cycle effect of the rapamycin disappeared after 1 day. Although the cell cycle was accelerated after cells escaped from the rapamycin inhibition after 1 day, the reduction of AD-related proteins was maintained.

Following rapamycin treatment, oxidative stress-induced apoptotic cell death in the cell line increased significantly (FIG. 2b). However, this was also accompanied by a significant lengthening of the G1 phase of the cell cycle (FIG. 3b). This effect was also short lasting, and the cells escaped inhibition after 1 day (FIG. 3b, compare d1 with d2). The rapamycin pre-treated cultures also showed increased tau phosphorylation and PHF formation under oxidative stress (FIG. 6b; FIG. 7b). Interestingly, this increase was followed by a decrease of these proteins, while the initial APP reduction was followed by a slight increase by day 2.

The addition of dexrazoxane to the cell cultures resulted in reduced cell numbers only after 2 days of treatment FIG. 1a). This delayed effect was more interesting since the dexrazoxane did not seem to protect cells against apoptotic cell death as efficiently as rapamycin did (FIG. 2a). The effects of the drug were due to an acceleration of the G1 phase of the cell cycle that was accompanied by little change in G2 time on day one and massive G2 lengthening on day 2 (FIGS. 3a and 4a). Although the drug increased the expression of all three AD-related proteins on the first day, by day two all three proteins were reduced in the cell lysates (FIGS. 5a, 6a, 7a).

Doxorubicin treatment on its own caused reduced cell numbers (FIG. 1a) mainly due to its cell cycle inhibitory effect, since it appeared to be protective against apoptosis (FIG. 2a). This cell cycle inhibitory effect was due mainly to the lengthening of the G2 phase of the cell cycle (FIG. 4a). The effect on G1 was reversed after 1 day (FIG. 3a), while the G2 inhibitory effect diminished (FIG. 4a). This phenomenon led to the elevated expression of APP (FIG. 5a) and PHF tau (FIG. 7a) despite the reduction of phospho-tau (FIG. 6a).

Rapamycin pre-treatment altered the effects of doxorubicin, in that it caused more apoptosis, and lead to a significant lengthening of both the G1 and G2 phases of the cycle after 1 day (FIG. 3c; FIG. 4c). Both effects were reversible and disappeared by day 2. The rapamycin pre-treatment also led to reduced APP and PHF tau formation that lasted after the cell cycle effects disappeared (FIG. 5c; FIG. 7c); the reduction of phospho tau by rapamycin pre-treatment disappeared after 1 day.

Dexrazoxane pre-treatment increased the G2 lengthening effect of doxorubicin (FIG. 4c), and led to the reduction of the APP and PHF-tau production while it did not significantly effect the phospho-tau production.

In summary, the lengthening of the G2 phase under the effect of doxorubicin, although it seems to be protective against apoptotic cell death, also leads to the elevation of AD-related protein expression.

Rapamycin does not seem to be an effective G1 inhibitor in this cell line, causing only a slight change in G1 time on its own. It causes a G2 delay more readily. This in turn is associated with protection against apoptosis and slight changes in the AD-related protein expression, reducing the hyperphosphorylated tau and slightly increasing APP production. Rapamycin pre-treatment is not protective against oxidative stress-induced damage but it accelerated it. However, in combination with doxorubicin it had strong protective effect against the accumulation of AD-related proteins, although the G1 inhibitory effects of such treatment were short-lived.

Dexrazoxane effectively reduced AD-related protein expression after two days in culture, however it did not confer protection against cell death on its own. Additionally, when followed by a doxorubicin-induced G2 inhibition, its protective effects against AD-related protein expression became more robust.

CONCLUSION

The results of this study provide evidence of the effectiveness of cell-cycle regulatory drugs, or combinations thereof, in reducing parameters of Alzheimer's disease pathology and protecting against oxidative stress-induced damage in a cell culture model of AD.

Each of the patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

The invention claimed is:

1. A method of reducing the accumulation of an Alzheimer's disease (AD)-related protein in a human Alzheimer's disease patient, wherein said method comprises:
   (a) administering to said patient a composition comprising rapamycin; and then
   (b) administering to said patient a composition comprising doxorubicin, wherein the amounts and sequential administration of said rapamycin and said doxorubicin reduce the level of an AD-related protein in neuronal cells of said patient, wherein said AD-related protein is selected from the group consisting of amyloid precursor protein (APP), AD-type hyperphosphorylated tau protein and AD-type paired helical filament (PHF) tau protein.

2. A method of reducing the accumulation of an Alzheimer's disease (AD)-related protein in a human Alzheimer's disease patient, wherein said method comprises:
   (a) administering to said patient a composition comprising dexrazoxane; and then
   (b) administering to said patient a composition comprising doxorubicin, wherein the amounts and sequential administration of said dexrazoxane and said doxorubicin reduce the level of an AD-related protein in neuronal cells of said patient, wherein said AD-related protein is selected from the group consisting of amyloid precursor protein (APP), AD-type hyperphosphorylated tau protein and AD-type paired helical filament (PHF) tau protein.

3. A method of reducing the expression of an Alzheimer's disease (AD)-related protein in a human Alzheimer's disease patient, wherein said method comprises:
   (a) administering to said patient a composition comprising rapamycin; and then
   (b) administering to said patient a composition comprising doxorubicin, wherein the amounts and sequential administration of said rapamycin and said doxorubicin reduce the level of an AD-related protein in neuronal cells of said patient, wherein said AD-related protein is selected from the group consisting of amyloid precursor protein (APP), AD-type hyperphosphorylated tau protein and AD-type paired helical filament (PHF) tau protein.

4. A method of reducing the expression of an Alzheimer's disease (AD)-related protein in a human Alzheimer's disease patient, wherein said method comprises:
   (a) administering to said patient a composition comprising dexrazoxane; and then
   (b) administering to said patient a composition comprising doxorubicin, wherein the amounts and sequential administration of said dexrazoxane and said doxorubicin reduce the level of an AD-related protein in neuronal cells of said patient, wherein said AD-related protein is selected from the group consisting of amyloid precursor protein (APP), AD-type hyperphosphorylated tau protein and AD-type paired helical filament (PHF) tau protein.

5. The method of any one of claims 1-4, wherein the AD-related protein is amyloid precursor protein (APP).

6. The method of any one of claims 1-4, wherein the AD-related protein is AD-type hyperphosphorylated tau protein.

7. The method of any one of claims 1-4, wherein the AD-related protein is AD-type paired helical filament (PHF) tau protein.

* * * * *